US011850065B2

(12) United States Patent
Yelin et al.

(10) Patent No.: US 11,850,065 B2
(45) Date of Patent: *Dec. 26, 2023

(54) VESSEL IMAGING SYSTEM AND METHOD

(71) Applicant: Technion Research & Development Foundation Limited, Haifa (IL)

(72) Inventors: Dvir Yelin, Haifa (IL); Lior Golan, Haifa (IL)

(73) Assignee: Technion Research & Development Foundation Limited, Haifa (IL)

(*) Notice: Subject to any disclaimer, the term of this patent is extended or adjusted under 35 U.S.C. 154(b) by 253 days.

This patent is subject to a terminal disclaimer.

(21) Appl. No.: 16/871,104

(22) Filed: May 11, 2020

(65) Prior Publication Data

US 2020/0268312 A1    Aug. 27, 2020

Related U.S. Application Data

(63) Continuation of application No. 14/373,358, filed as application No. PCT/IB2013/050442 on Jan. 17, 2013, now Pat. No. 10,646,160.

(60) Provisional application No. 61/588,631, filed on Jan. 19, 2012.

(51) Int. Cl.
    *A61B 5/00*    (2006.01)
    *A61B 5/02*    (2006.01)
    *A61B 5/145*   (2006.01)

(52) U.S. Cl.
    CPC .......... *A61B 5/489* (2013.01); *A61B 5/0066* (2013.01); *A61B 5/0075* (2013.01); *A61B 5/02007* (2013.01); *A61B 5/0068* (2013.01); *A61B 5/0084* (2013.01); *A61B 5/14546* (2013.01); *A61B 5/418* (2013.01)

(58) Field of Classification Search
    None
    See application file for complete search history.

(56) References Cited

U.S. PATENT DOCUMENTS

| 5,371,368 A | 12/1994 | Alfano et al. |
| 5,436,655 A | 7/1995 | Hiyama et al. |
| 5,693,043 A | 12/1997 | Kittrell et al. |
| 6,006,001 A | 12/1999 | Alfano et al. |

(Continued)

FOREIGN PATENT DOCUMENTS

| JP | 2007-127860 | 5/2007 |
| WO | WO 2004/044562 | 5/2004 |

(Continued)

OTHER PUBLICATIONS

Applicant-Initiated Interview Summary dated Aug. 2, 2019 From the US Patent and Trademark Office Re. U.S. Appl. No. 14/373,358. (4 pages).

(Continued)

*Primary Examiner* — Katherine L Fernandez

(57) ABSTRACT

A method for locating a vessel, the method comprising illuminating at least a portion of the vessel with a background light having a substantially high susceptibility to absorption by particles in said portion of the vessel; detecting backscattered light from said illuminated portion of the vessel; reproducing an image from said backscattered light; and identifying dark regions within said reproduced image.

27 Claims, 23 Drawing Sheets
(7 of 23 Drawing Sheet(s) Filed in Color)

(56) References Cited

U.S. PATENT DOCUMENTS

| | | | |
|---|---|---|---|
| 6,119,031 A * | 9/2000 | Crowley | G01J 3/36 600/407 |
| 6,554,775 B1 | 4/2003 | Peyman et al. | |
| 6,621,917 B1 | 9/2003 | Vilser | |
| 7,904,138 B2 | 3/2011 | Goldman et al. | |
| 2003/0048540 A1 | 3/2003 | Xie et al. | |
| 2004/0212808 A1 * | 10/2004 | Okawa | A61B 5/0066 356/479 |
| 2006/0134002 A1 | 6/2006 | Lin | |
| 2006/0142662 A1 | 6/2006 | Van Beek | |
| 2006/0241364 A1 * | 10/2006 | Ince | G01N 21/6428 600/323 |
| 2007/0188855 A1 | 8/2007 | Shishkov et al. | |
| 2008/0021329 A1 | 1/2008 | Wood et al. | |
| 2008/0045817 A1 * | 2/2008 | Van Beek | A61B 5/0059 600/310 |
| 2008/0097225 A1 | 4/2008 | Tearney et al. | |
| 2009/0318759 A1 | 12/2009 | Jacobsen et al. | |
| 2010/0027020 A1 | 2/2010 | Nebosis | |
| 2010/0045778 A1 | 2/2010 | Yelin | |
| 2011/0044910 A1 * | 2/2011 | Lin | A61B 5/0071 424/9.6 |
| 2013/0163077 A1 | 6/2013 | Neuberg | |
| 2015/0011896 A1 | 1/2015 | Yelin et al. | |

FOREIGN PATENT DOCUMENTS

| | | |
|---|---|---|
| WO | WO 2008/005282 | 6/2008 |
| WO | WO 2009/037432 | 3/2009 |
| WO | WO 2013/108209 | 7/2013 |

OTHER PUBLICATIONS

Applicant-Initiated Interview Summary dated Nov. 30, 2018 From the US Patent and Trademark Office Re. U.S. Appl. No. 14/373,358. (4 pages).

Communication Pursuant to Rule 164(1) EPC [Supplementary Partial European Search Report] dated Aug. 31, 2015 From the European Patent Office Re. Application No. 13738761.9.

International Preliminary Report on Patentability dated Jul. 31, 2014 From the International Bureau of WIPO Re. Application No. PCT/IB2013/050442.

International Search Report and the Written Opinion dated May 28, 2013 From the International Searching Authority Re. Application No. PCT/IB2013/050442.

Official Action dated Apr. 7, 2017 From the US Patent and Trademark Office Re. U.S. Appl. No. 14/373,358. (31 pages).

Official Action dated Aug. 9, 2018 From the US Patent and Trademark Office Re. U.S. Appl. No. 14/373,358. (23 pages).

Official Action dated Jul. 10, 2012 From the US Patent and Trademark Office Re. U.S. Appl. No. 12/461,558.

Official Action dated Dec. 15, 2017 From the US Patent and Trademark Office Re. U.S. Appl. No. 14/373,358. (19 pages).

Official Action dated Apr. 18, 2019 From the US Patent and Trademark Office Re. U.S. Appl. No. 14/373,358. (22 pages).

Official Action dated Aug. 21, 2013 From the US Patent and Trademark Office Re. U.S. Appl. No. 12/461,558.

Official Action dated Jan. 26, 2012 From the US Patent and Trademark Office Re. U.S. Appl. No. 12/461,558.

Partial European Search Report and the European Search Opinion dated Jan. 13, 2010 From the European Patent Office Re. Application No. 09010571.9.

Restriction Official Action dated Sep. 8, 2016 From the US Patent and Trademark Office Re. U.S. Appl. No. 14/373,358.

Supplementary European Search Report and the European Search Opinion dated Jan. 4, 2016 From the European Patent Office Re. Application No. 13738761.9.

Bishop et al. "Effect of Erythrocyte Aggregation on Velocity Profiles in Venules", American Journal of Physiology, Heart and Circulatory Physiology, 280(1): H222-H236, Jan. 2001.

Golan et al. "Flow Cytometry Using Spectrally Encoded Confocal Microscopy", Optics Letters, 35(13): 2218-2220, Jul. 1, 2010.

Golan et al. "High-Speed Interferometric Spectrally Encoded Flow Cytometry", Optics Letters, 37(24): 5154-5156, Dec. 15, 2012.

Golan et al. "Noninvasive Imaging of Flowing Blood Cells Using Label-Free Spectrally Encoded Flow Cytometry", Biomedical Optics Express, XP055202682, 3(6): 1455-1464, Jun. 1, 2012. p. 1458, Lines 22-30, Fig.2.

Hoffbrand et al. "Erythropoiesis and General Aspects of Anaemia". "The White Cells 1: Granulocytes, Monocytes and Their Benign Disorders", Essential Haematology, Chap.2 and 7: 18 and 94, 1980 ff.

Konstantinopoulos et al. "Venous Levels of Shear Support Neutrophil-Platelet Adhesion and Neutrophil Aggregation in Blood Via P-Selection and Beta2-Integrin", Circulation, 98: 873-882, Nov. 1, 1998.

Motz et al. "Spectral- and Frequency-Encoded Fluorescence Imaging", Optics Letters, XP001235409, 30(20): 2760-2762, Oct. 15, 2005. p. 2760, 1-h Col., § 2-p. 2762, 1-h Col., § 1.

Schmid-Schoenbein et al. "The Interaction of Leukocytes and Erythrocytes in Capillary and Postcapillary Vessels", Microvascular Research, 19: 45-70, 1980.

Yelin et al. "Three-Dimensional Miniature Endoscopy.A Single Optical Fibre Acts as A Flexible Probe to Transmit A Superior Image of An Internal Landscape", Nature, XP002558589, 443(7113): 765, Oct. 19, 2006.

Yelin et al. "Volumetric Sub-Surface Imaging Usding Spectrally Encoded Endoscopy", Optics Express, 16(3): 1748-1757, Feb. 4, 2008.

* cited by examiner

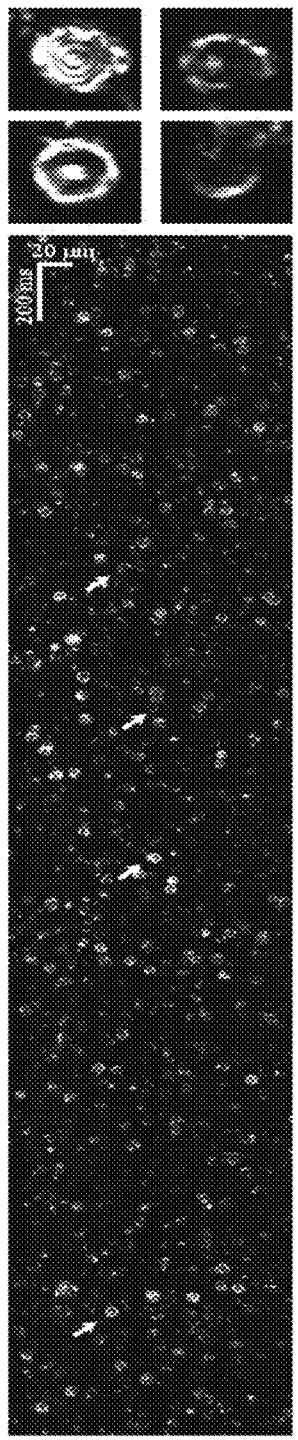
FIG. 17A
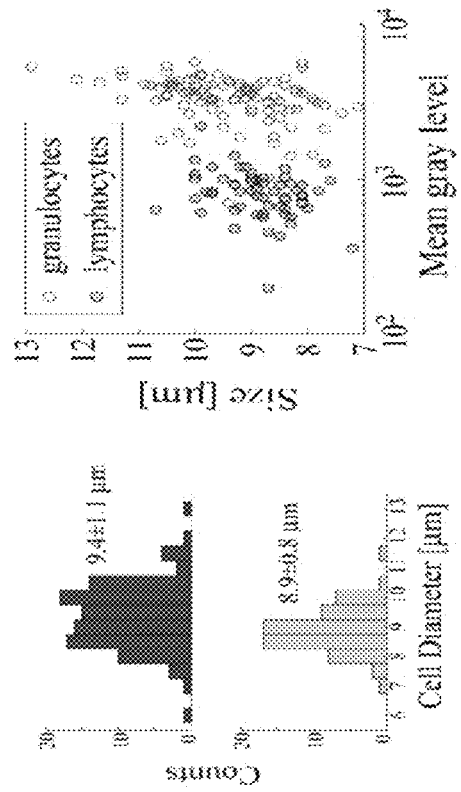
FIG. 17C
FIG. 17D
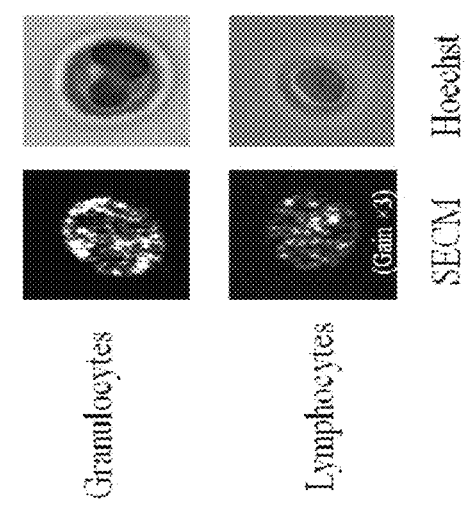
FIG. 17B

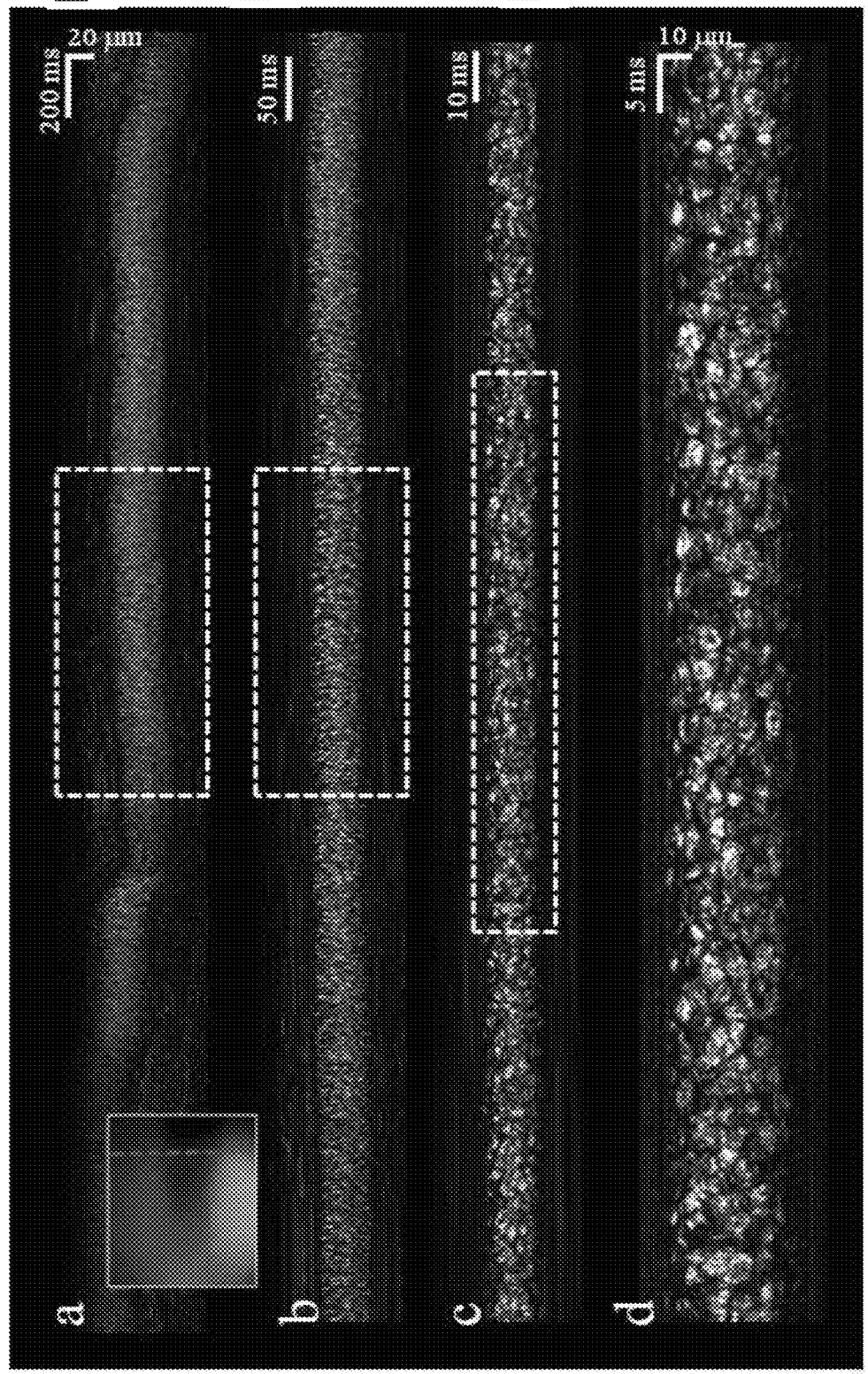

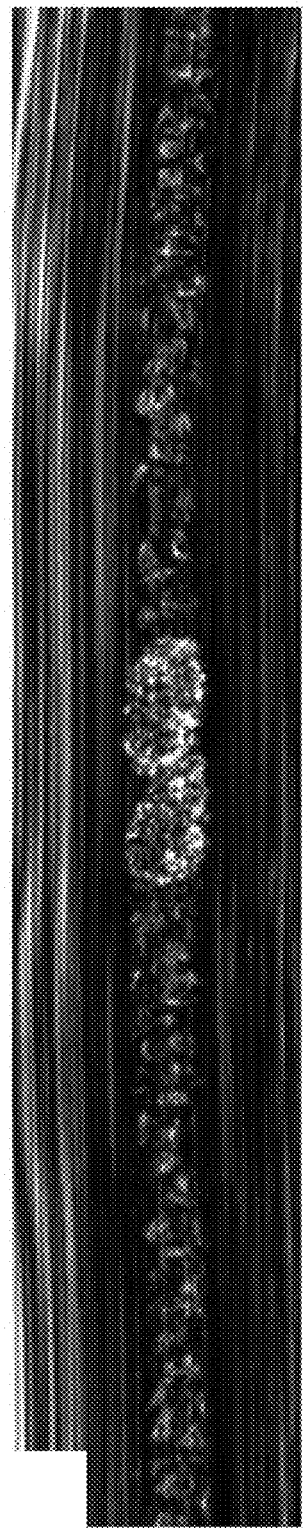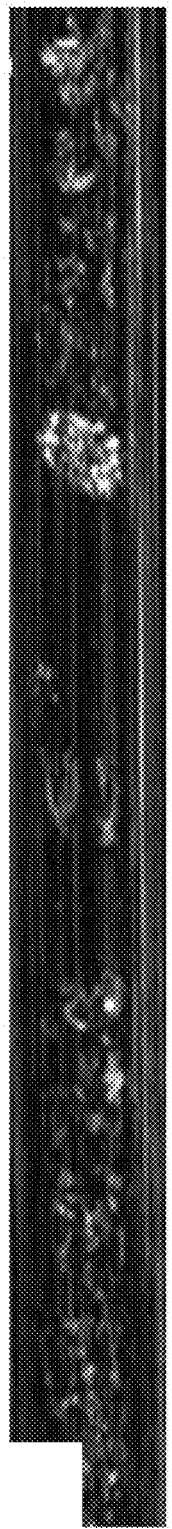
FIG. 21A
FIG. 21B
FIG. 21C

VESSEL IMAGING SYSTEM AND METHOD

RELATED APPLICATIONS

This application is a Continuation of U.S. patent application Ser. No. 14/373,358 filed on Jul. 20, 2014, which is a National Phase of PCT Patent Application No. PCT/IB2013/050442 having International Filing Date of Jan. 17, 2013, which claims the benefit of priority under 35 USC § 119(e) of U.S. Provisional Patent Application No. 61/588,631 filed on Jan. 19, 2012. The contents of the above applications are all incorporated by reference as if fully set forth herein in their entirety.

FIELD AND BACKGROUND OF THE INVENTION

The present invention, in some embodiments thereof, relates to imaging devices and, more particularly, but not exclusively, to imaging system and methods for scientific and medical applications.

Endoscopic confocal microscopy devices are extensively used in minimally invasive medical diagnosis to look below tissue surfaces and for intervention purposes. Confocal microscopy is a technique generally used to acquire an image of a specimen and is based on focusing illuminating light from a point source to a point on the specimen, and focusing emitted light (responsive to the illuminating light) from the illuminated point on the specimen unto a small pinhole in an opaque screen. As only the emitted light from the illuminated point is focused unto the hole, the emitted light passes through the pinhole while all other light not emitted by the point is substantially blocked out. A detector on the other side of the screen detects the amount of emitted light passing through the pinhole and quantifies the amount for image reproduction purposes. As only one point in the specimen is illuminated at a time, two-dimensional (2D) or three-dimensional (3D) imaging generally is done by scanning over a regular raster (a rectangular pattern of parallel scanning lines) in the specimen.

A technique generally used to integrate confocal microscopy inside probes used in medical and scientific applications such as, for example, endoscopic probes and catheters, is spectrally encoded confocal microscopy (SECM). In SECM, the specimen is generally scanned line by line, with illuminating light at a different wavelength hitting each point along a line (each point on a line is "encoded" by a different wavelength). Emitted light from each point (each point emitting light at a different wavelength) is detected by a detector and, spatial information of the specimen along the line may be decoded by measuring the detected wavelengths. A 2D image may be reproduced by relatively slowly scanning the encoded lines mechanically within the probe.

An alternative technique to SECM is spectrally encoded endoscopy (SEE). SEE described in "Volumetric sub-surface imaging using spectrally encoded endoscopy", by D. Yelin et al, Optics Express 1750/Vol. 16, No. 3/4 Feb. 2008; as follows: "Spectrally encoded endoscopy (SEE) [7] is a recently developed technique that utilizes wavelength to encode transverse image information. The SEE probe, comprising a single optical fiber, a diffraction grating, and a low NA lens, focuses spectrally dispersed light onto the sample. In turn, each point along this line is illuminated by a distinct spectral band. Each line of the image is acquired by measuring the spectrum of light reflected from the sample and returned back through the SEE probe using a high-speed spectrometer that resides outside the body. The second dimension of the image is obtained by moving the fiber at slow rates (e.g. 30 Hz). Without the need for rapid transverse scanning at the distal end of the endoscope, SEE allows video rate imaging to be performed through a miniature (i.e. 350 μm diameter) endoscopic device [13]. When the SEE probe is placed in the sample arm of an interferometer, it additionally can achieve three-dimensional topological, surface imaging in real-time, by use of time [14] and spectral [13, 15] domain low coherence interferometry."

Use of SECM for spectrally encoded imaging of flowing blood cells is further described in "Flow cytometry using spectrally encoded confocal microscopy", by D. Yelin and L. Golan, Optics, Volume 35, Issue 13, 2218-2220 (2010), which relates to "Flow cytometry techniques often rely on detecting fluorescence from single cells flowing through the cross section of a laser beam, providing invaluable information on vast numbers of cells. Such techniques, however, are often limited in their ability to resolve clusters of cells or parallel cell flow through large vessels. We present a confocal imaging technique that images unstained cells flowing in parallel through a wide channel, using spectrally encoded reflectance confocal microscopy that does not require mechanical scanning. Images of red blood cells from our system are compared to conventional transmission microscopy, and imaging of flowing red blood cells in vitro is experimentally demonstrated."

It is known that green light is more susceptible to absorption by blood compared to the other colors in the light spectrum. This makes green light an important component for detecting blood vessels in the body. U.S. Publication No. 2008/0045817 to Van Beek et al describes, "Provided is a method and an apparatus for detection of objects below the surface of diffuse scattering media, in particular blood capillaries in organs such as the skin of human beings, using Orthogonal Polarized Spectral Imaging (OPSI), according to the invention comprising the steps of: imaging the object in question at least two different angles so as to obtain a shift of position in the imaging plane; and subsequently comparing relative shifts of objects in the two images so as to obtain coordinates of the imaged objects with respect to the organ surface."

SUMMARY OF THE INVENTION

According to an aspect of some embodiments of the present invention, there is provided a method for locating a vessel, the method comprising: illuminating at least a first sub-region of a region including at least a portion of the vessel with illuminating light comprising a background light component having a substantially high susceptibility to absorption by particles in said portion of the vessel; detecting returned or emitted light from said illuminated sub-region; reproducing at least one image from said returned or emitted light; identifying higher-absorbing regions within said reproduced image; moving the illumination to a second or further sub-region when a higher-absorbing region corresponding to said portion of the vessel is not so-identified; and iteratively applying said steps of illuminating, detecting, reproducing, identifying, and moving, until said higher-absorbing region is identified.

According to some embodiments of the present invention, said first or said second or further sub-region is small enough that it has at least a 50% chance of not including a blood vessel.

According to some embodiments of the present invention, the region receiving said illuminating light and returning said detected returned or emitted light is selected by the placement of an imaging probe.

According to some embodiments of the present invention, said probe is small enough to be hand-held.

According to some embodiments of the present invention, said method comprises detecting particles within said higher-absorbing regions.

According to some embodiments of the present invention, said method comprises acquiring at least a portion of an image of a cross-section of said portion of the vessel, and one or more particles within.

According to some embodiments of the present invention, said illuminating light comprises a broad bandwidth light or a wavelength-swept light component.

According to some embodiments of the present invention, said method comprises spectrally dispersing at least said broad bandwidth light or wavelength-swept light component of said illuminating light along an axis including said vessel.

According to some embodiments of the present invention, said method comprises determining a location, a speed of flow, a size, a length, a shape, a color, an orientation, a brightness of a particle, a number of particles, or any combination thereof, in said portion of said vessel.

According to some embodiments of the present invention, said vessel is a capillary, a vein or an artery.

According to some embodiments of the present invention, said absorbable background light component includes a green light.

According to some embodiments of the present invention, said vessel is located at a depth up to 100 μm below a tissue surface.

According to some embodiments of the present invention, said vessel is located at a depth of up to 200 μm below a tissue surface.

According to some embodiments of the present invention, said method comprises substantially minimizing tissue movement.

According to some embodiments of the present invention, said method comprises displaying at least one of said images to a viewer.

According to an aspect of some embodiments of the present invention, there is provided a system for locating a vessel, the system comprising: a light source for generating a background light which has substantially high susceptibility to absorption by particles in said vessel; an imaging probe adapted to illuminate at least a portion of said vessel with said background light; a detection unit for detecting returned or emitted light from said illuminated portion of said vessel; and a processor unit for reproducing at least one image of said illuminated portion of the vessel from said returned or emitted light.

According to some embodiments of the present invention, said imaging probe is adapted to be held in one hand.

According to some embodiments of the present invention, the field of view illuminated with said background light and from which said returned or emitted light is detected with said detection unit is small enough that it has at least a 50% chance of not including a blood vessel.

According to some embodiments of the present invention, said probe captures said returned or emitted light from said illuminated portion of the vessel.

According to some embodiments of the present invention, said imaging probe includes a beam combiner.

According to some embodiments of the present invention, said system comprises a broad bandwidth light source or a wavelength-swept light source with output directed to the imaging probe through the beam combiner to provide illuminating light for at least a sub-portion of said portion of said vessel.

According to some embodiments of the present invention, the range of center wavelengths produced by said broad bandwidth light source or said wavelength-swept light source is between 800 and 1300 nm wide, with a bandwidth between 10 to 300 nm.

According to some embodiments of the present invention, said system includes a dispersing element for spectrally dispersing said illuminating light along an axis of the vessel.

According to some embodiments of the present invention, said processor reproduces an image of a cross-section of said illuminated portion of the vessel.

According to some embodiments of the present invention, said image of the cross-section of said vessel comprises a cross-section of one or more particles in said portion of the vessel.

According to some embodiments of the present invention, said probe includes an objective lens for focusing said illuminating light.

According to some embodiments of the present invention, said system includes an interferometric apparatus, wherein light returned or emitted from said vessel upon illumination by said broad bandwidth light source or wavelength-swept light source is brought together with a reference light from said broad bandwidth light source or wavelength-swept light source before being directed to said detection unit.

According to some embodiments of the present invention, said background light source transmits a wide-field light.

According to some embodiments of the present invention, said background light source transmits a green light.

According to some embodiments of the present invention, said background light source, said detection unit, or said processor, or any combination thereof, is included in said imaging probe.

According to some embodiments of the present invention, said imaging probe is adapted to illuminate and image said portion of the vessel at a depth up to 100 μm below a tissue surface.

According to some embodiments of the present invention, said imaging probe is adapted to illuminate and image said portion of the vessel at a depth up to 200 μm below a tissue surface.

According to some embodiments of the present invention, an imaging probe for locating a vessel is provided, the probe comprising optical elements for illuminating a portion of said vessel with a light comprising a first absorbable light component having a substantially greater absorption by particles in the vessel than a second illuminating light component; wherein said optical elements include: a dispersing element for spectrally dispersing at least said second illuminating light component along an axis of the vessel; and a collimator for shaping the beam of returned or emitted light from said illuminated portion of the vessel.

According to some embodiments of the present invention, said probe includes a light source for generating said first absorbable light component.

According to some embodiments of the present invention, said probe includes a light source for generating said second illuminating light component.

According to some embodiments of the present invention, said probe includes a detection unit for detecting said returned or emitted light from said illuminated portion of the vessel.

According to some embodiments of the present invention, said probe includes a processor unit for reproducing at least one image of said illuminated portion of the vessel from said returned or emitted light.

According to some embodiments of the present invention, said probe includes an optical bundle for transmitting said returned or emitted light to a detection unit external to the probe.

According to some embodiments of the present invention, said probe includes an arrangement of lenses comprising a telescopic light relay between said dispersing element and elements of said probe proximal to said vessel.

According to some embodiments of the present invention the dispersing element includes a combining element.

According to an aspect of some embodiments of the present invention, there is provided a method for locating a vessel in a subject's body, the method comprising: pressing an imaging probe providing a background light source against said subject's tissue; removing said imaging probe from said subject's tissue following detection; viewing a display of an image of the blood vessel.

According to an aspect of some embodiments of the present invention, there is provided an apparatus for imaging particles in flow, the apparatus comprising: a wavelength-swept light source producing a first beam and a second beam; optical elements to which the output of said first beam is directed, producing a spectrally dispersed light along a cross-section of the stream of said particles in flow; an interferometric apparatus which combines a sample beam, comprising light returned from the region of said cross-section, with a reference beam, comprising said second beam; a detection unit for detecting the light of said combined sample and reference beams; and a processor unit for reproducing an image of said region of said cross-section.

According to some embodiments of the present invention, said imaged particles are contained within a capillary, artery, or vein in a subject's body.

According to some embodiments of the present invention, said processor unit decodes the spatial information carried by said combined sample and reference beams by demodulating data received by said detector unit using a discrete Hilbert transform.

According to some embodiments of the present invention, said image comprises one or more lines, said lines representing data taken during different sweeps of said wavelength-swept light source.

According to some embodiments of the present invention, the frequency with which frequency sweeps occur is above 10 KHz.

According to an aspect of some embodiments of the present invention, there is provided a system for imaging particles in flow, the system comprising: a broad-spectrum light source; optical elements to which the output of said first beam is directed, producing a spectrally dispersed light along a cross-section of the stream of said particles in flow; a detection unit configured to detect said spectrally dispersed light returned from said particles in flow; and a processor unit which determines a color or spectral property characterization of said particles in flow using input from said detection unit.

According to some embodiments of the present invention, said processor unit determines a color or spectral property characterization by combining samples from said detection unit corresponding to light returned from a plurality of said particles in flow intersecting a plurality of locations along said cross-section.

According to some embodiments of the present invention, said particles in flow are contained within a capillary, artery, or vein in a subject's body.

According to some embodiments of the present invention, said combining of samples includes integration of a plurality of samples received at a plurality of times from a plurality of said particles in flow, said integration being performed for a plurality of wavelength ranges to produce a plurality of integrated values.

According to some embodiments of the present invention, said combining of samples includes normalization of said integrated values according to the number of samples comprising each, to produce averages.

According to some embodiments of the present invention, said optical elements are adjustable to disperse light across a cross-section of said stream of particles in flow which is non-orthogonal to the direction of flow.

According to some embodiments of the present invention, said optical elements are adjustable to disperse light across an adjustable width.

According to some embodiments of the present invention, the background light component includes a wide-field light.

According to some embodiments of the present invention, the method comprises coupling the backscattered light to an optical waveguide.

According to some embodiments of the present invention, the image of the illuminated portion of the portion of the vessel is a two-dimensional (2D) image.

According to some embodiments of the present invention, the method comprises collimating the illuminating light prior to spectrally dispersing the light.

According to some embodiments of the present invention, the method comprises magnifying the dark regions within the reproduced image.

According to some embodiments of the present invention, the method comprises identifying particles within the dark regions.

According to some embodiments of the present invention, the method comprises sending the background light through a multi-mode optical fiber.

According to some embodiments of the present invention, the method comprises sending the illuminating light through a single mode optical fiber.

According to some embodiments of the present invention, the method comprises diffracting the illuminating light for combining with the background light.

According to some embodiments of the present invention, the probe captures the backscattered light from the illuminated portion of the vessel.

According to some embodiments of the present invention, the system includes a collimator for collimating the backscattered light prior to detection.

According to some embodiments of the present invention, the system includes a diffraction grating for spectrally dispersing an illuminating light along an axis of the vessel.

According to some embodiments of the present invention, the imaging probe includes a beam combiner.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and the images makes apparent to those skilled in the art how embodiments of the invention may be practiced.

In the drawings:

Figure 1:
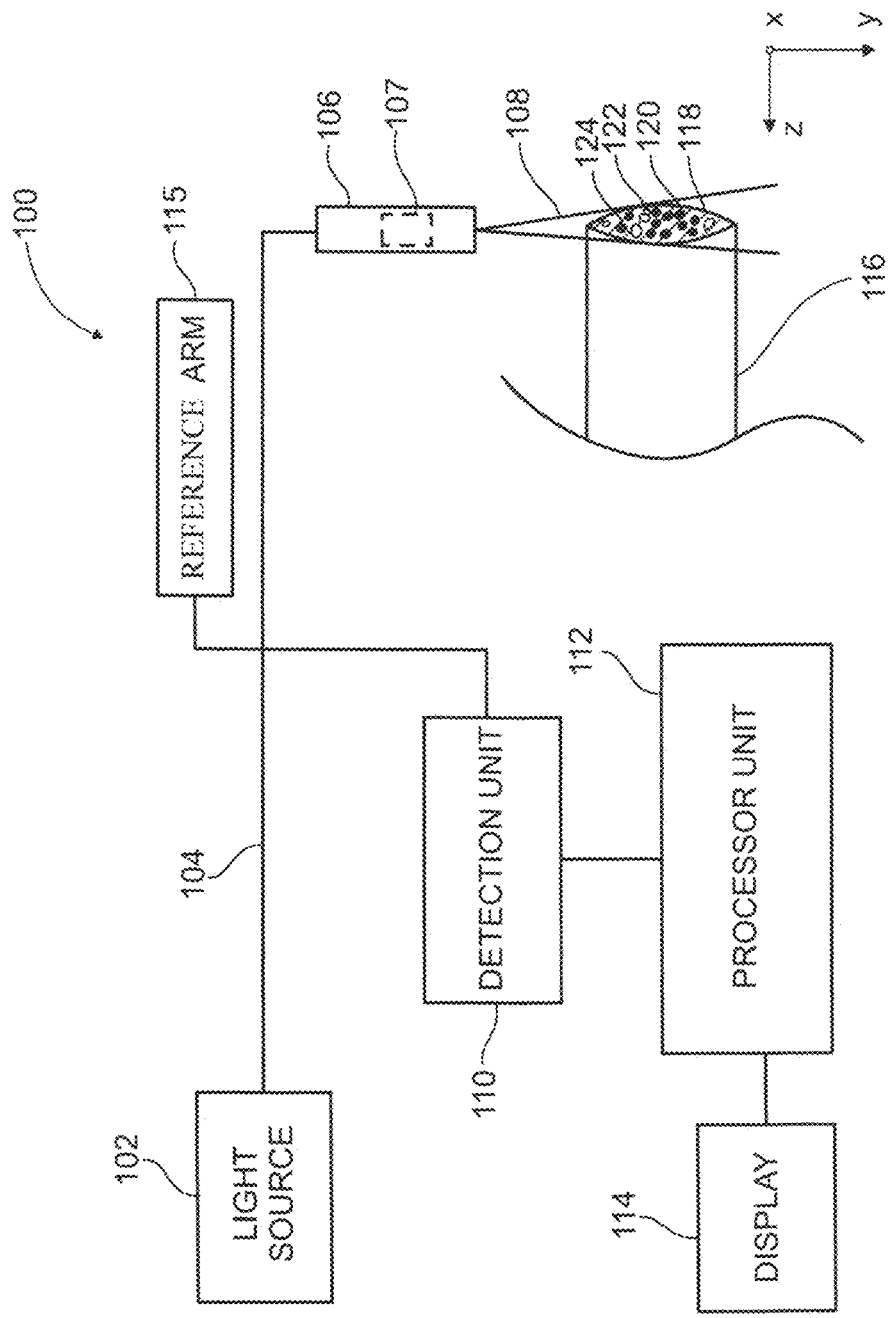
Figure 2:
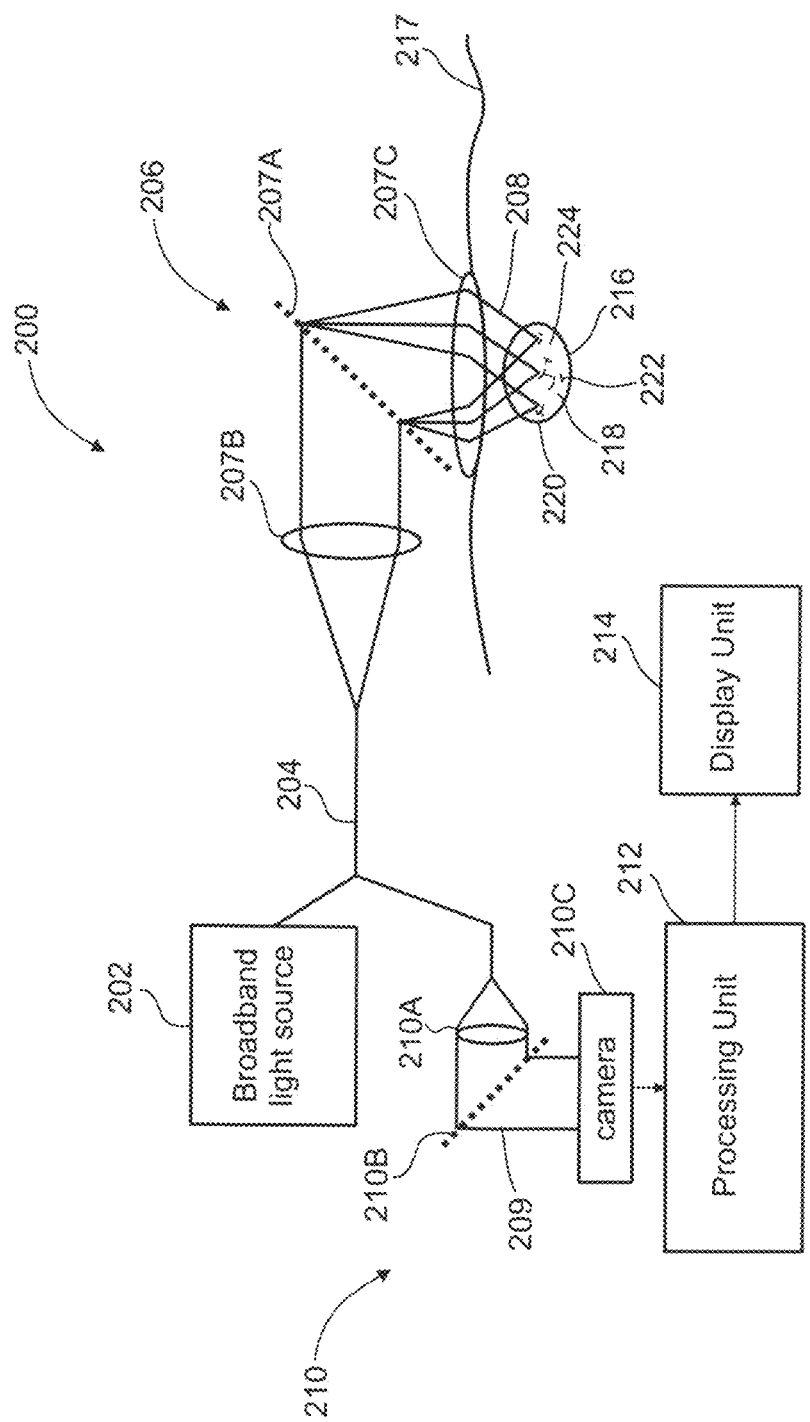
Figure 3:
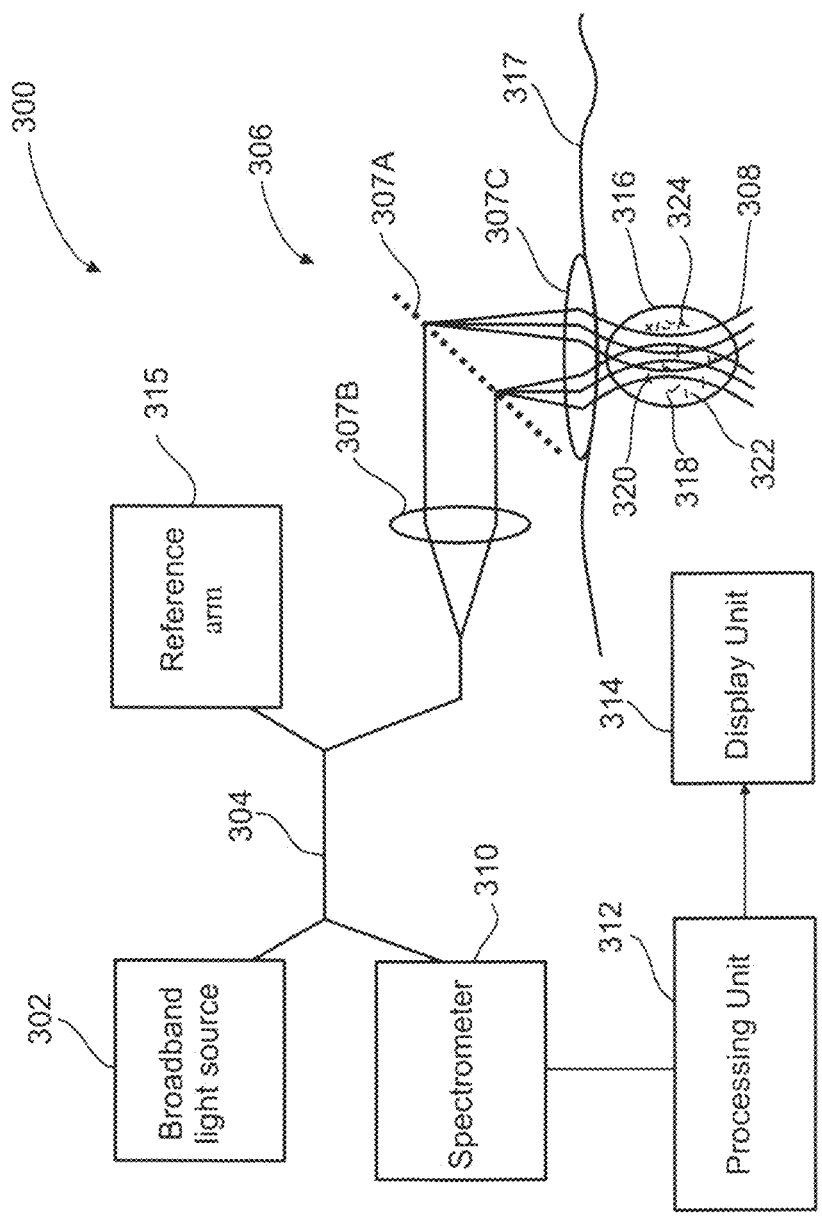
Figure 4:
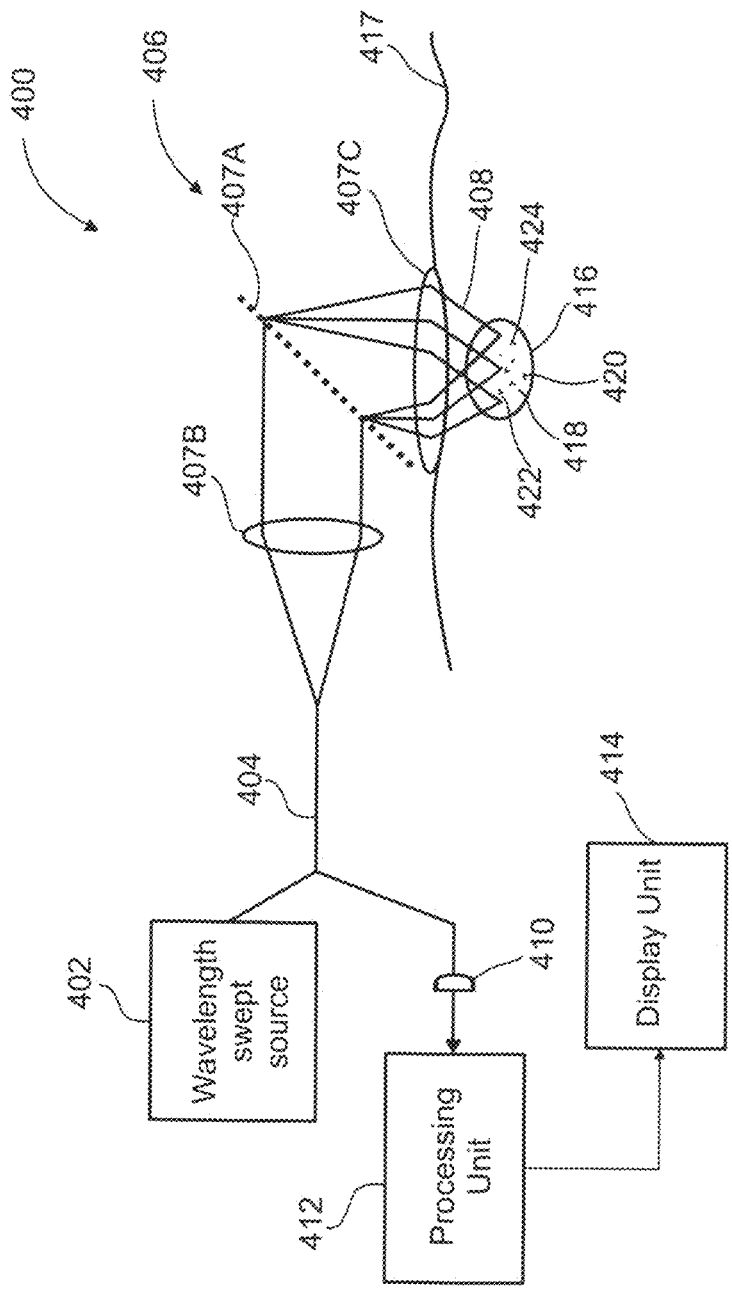
Figure 5:
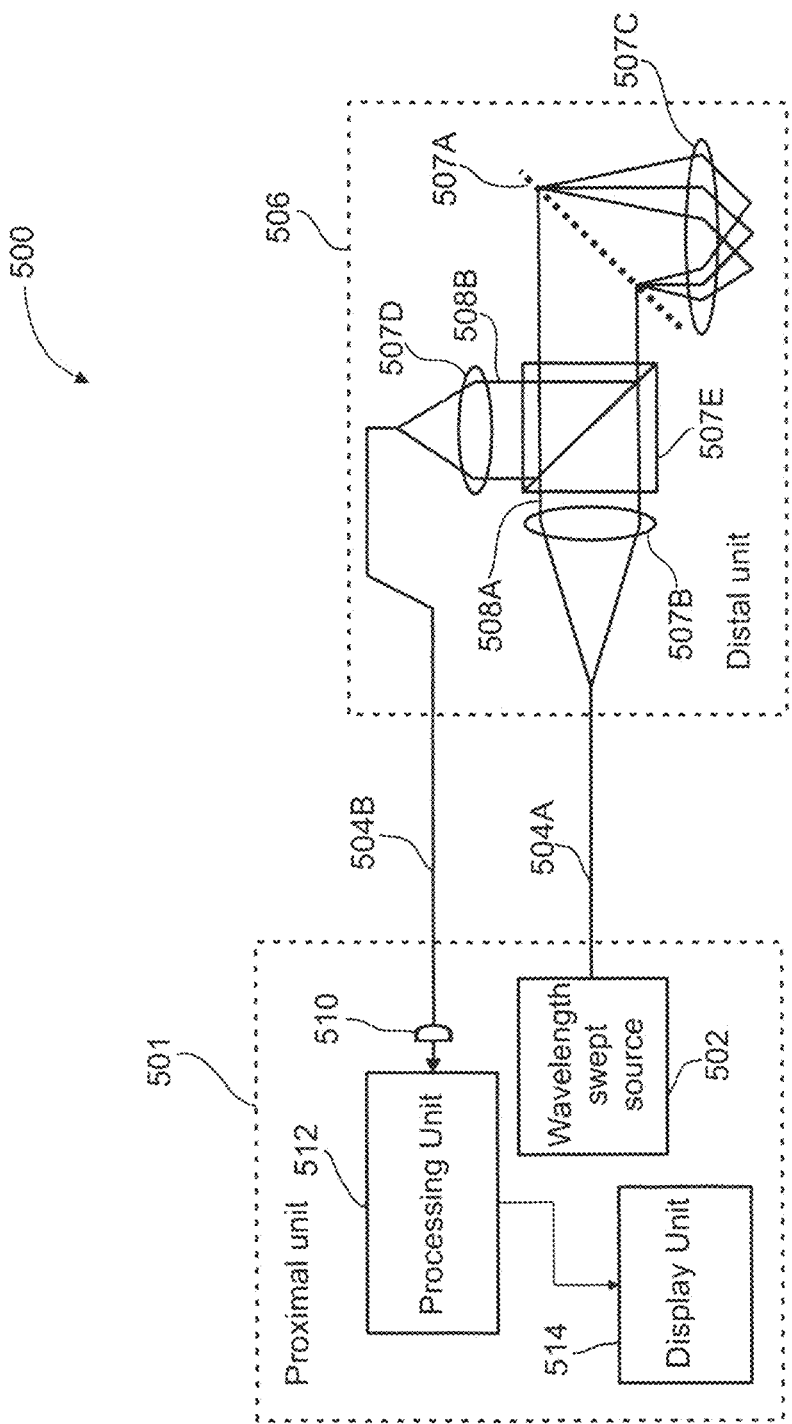
Figure 6:
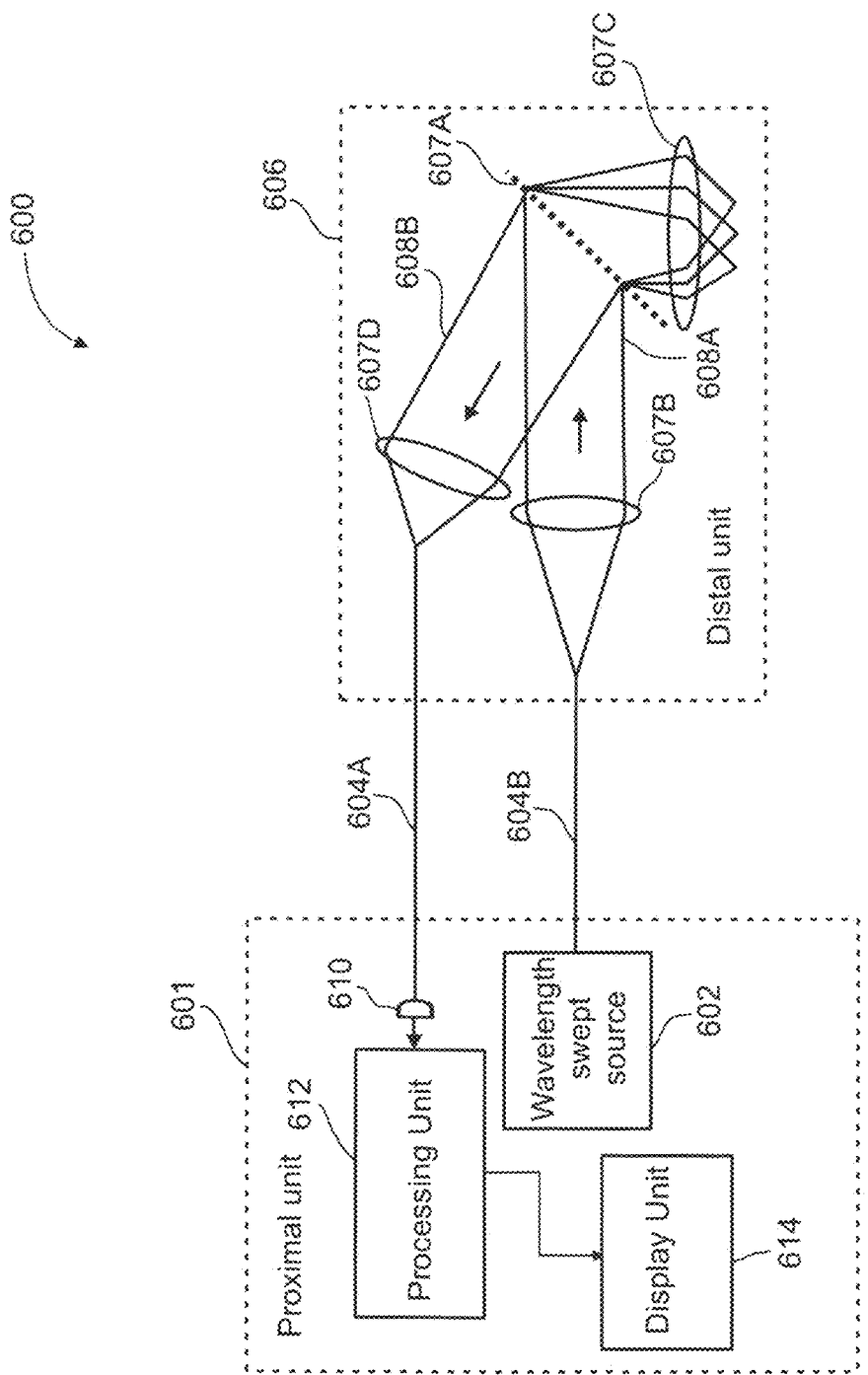
Figure 7B:
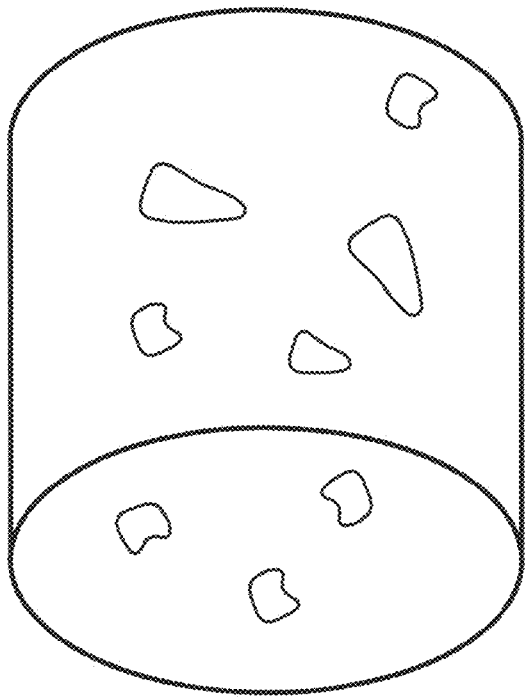
Figure 7A:
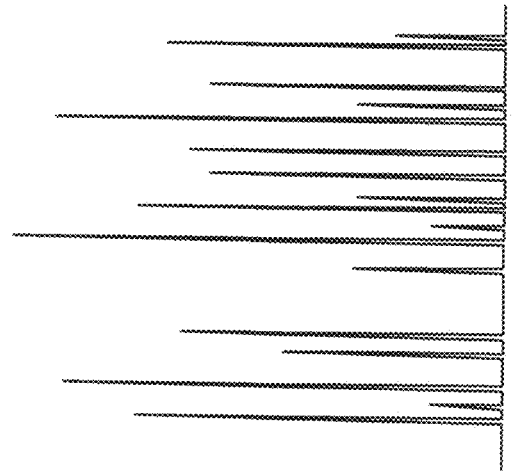
Figure 8A:
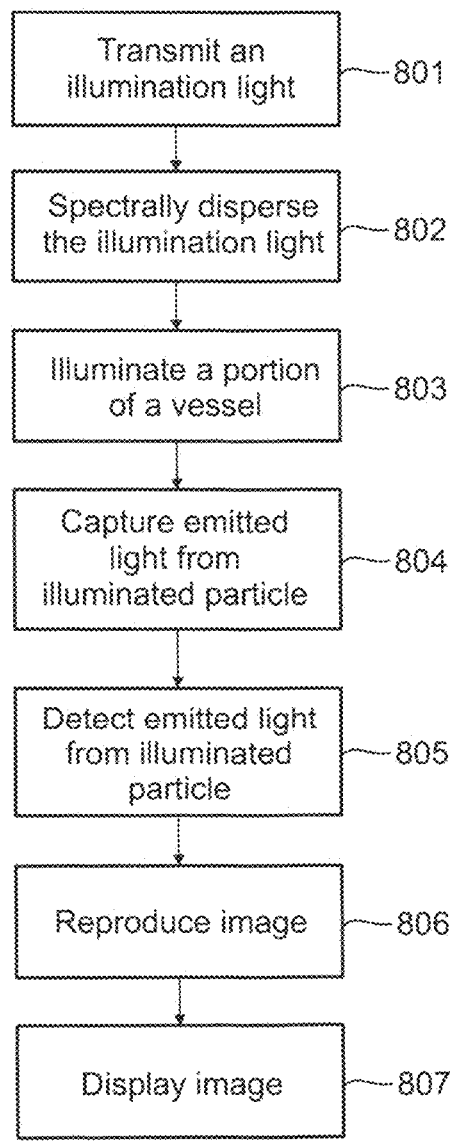
Figure 8B:
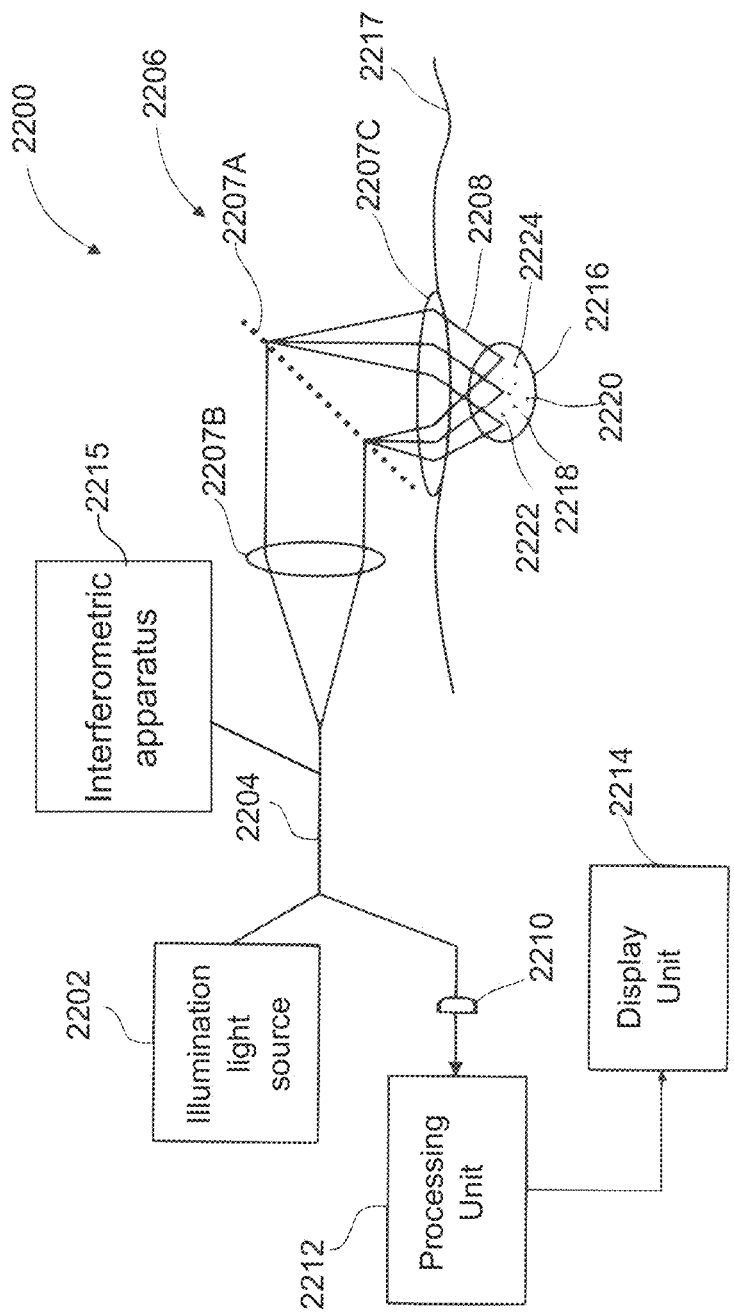
Figure 9:
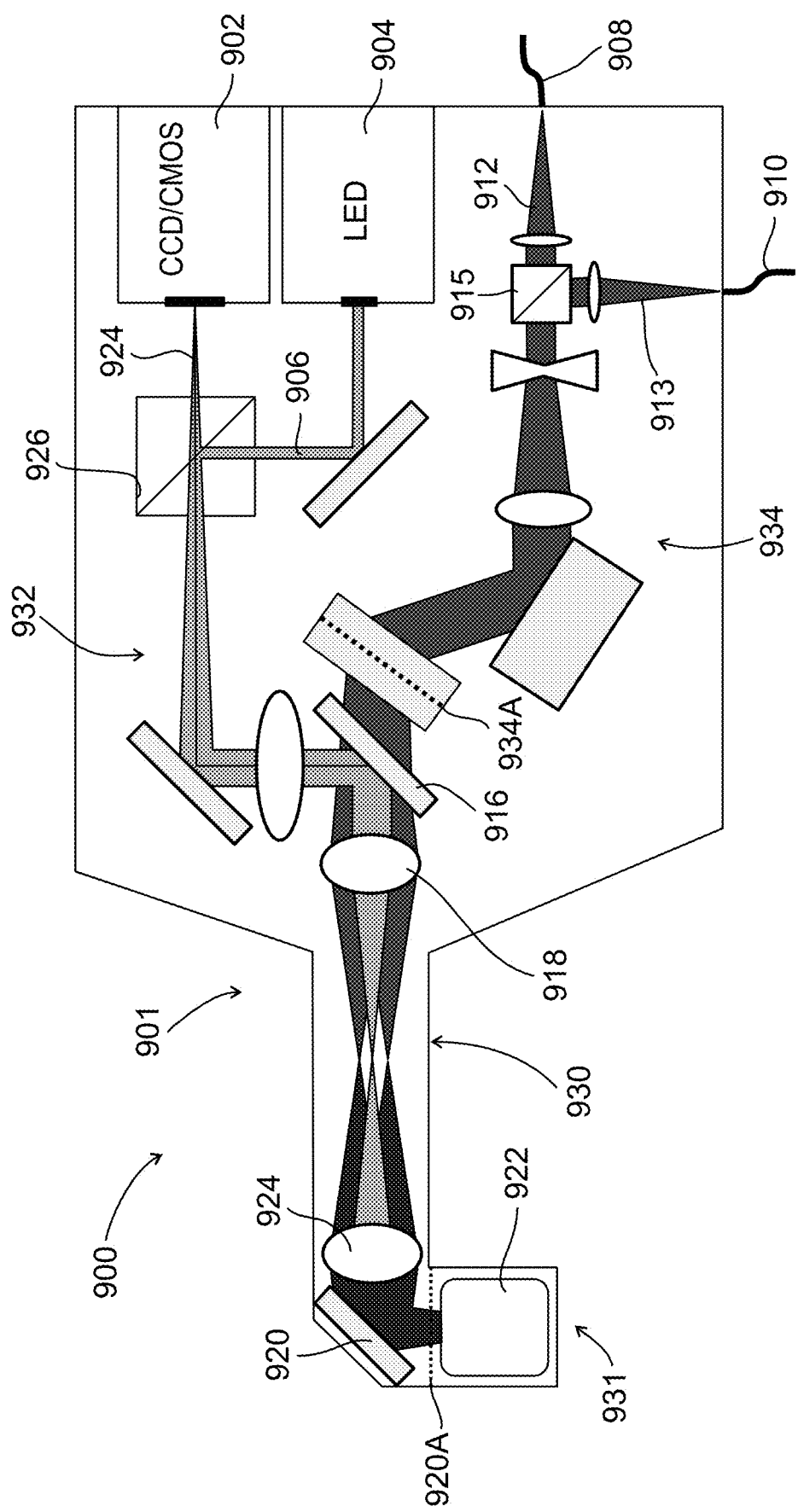
Figure 10:
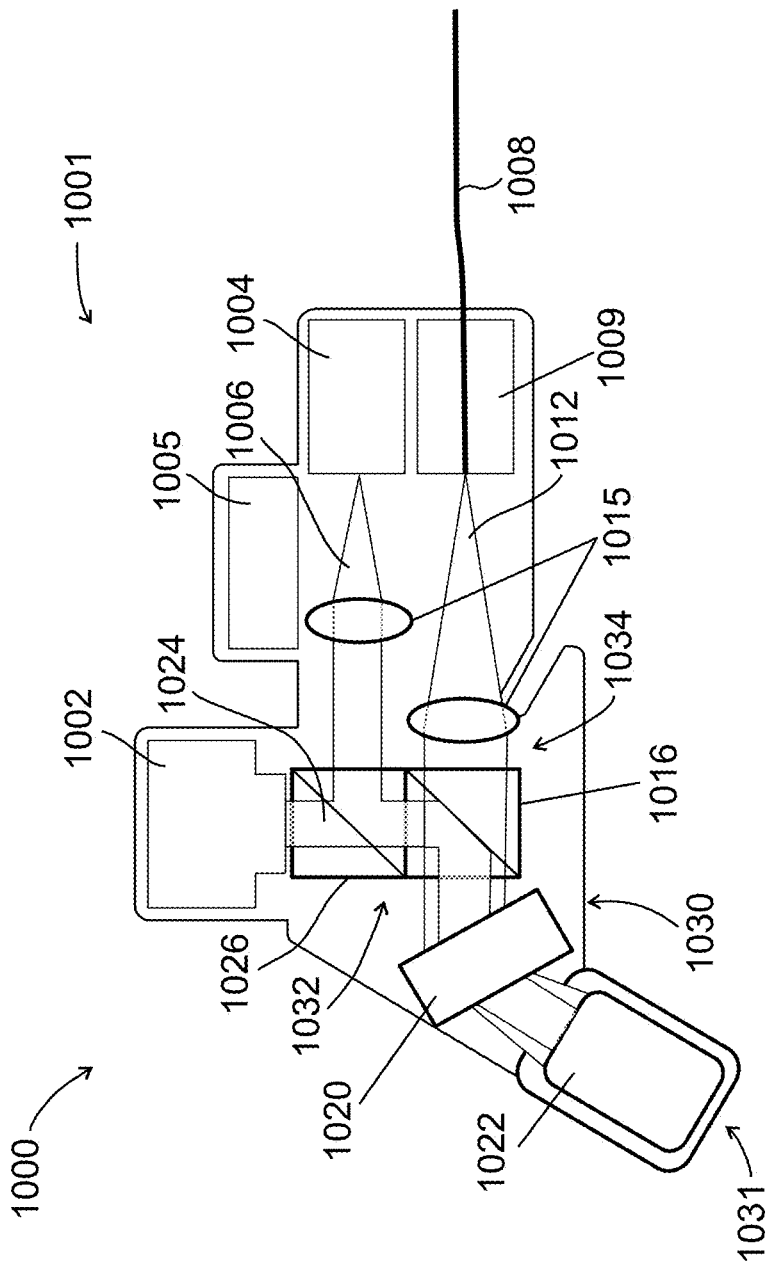
Figure 11:
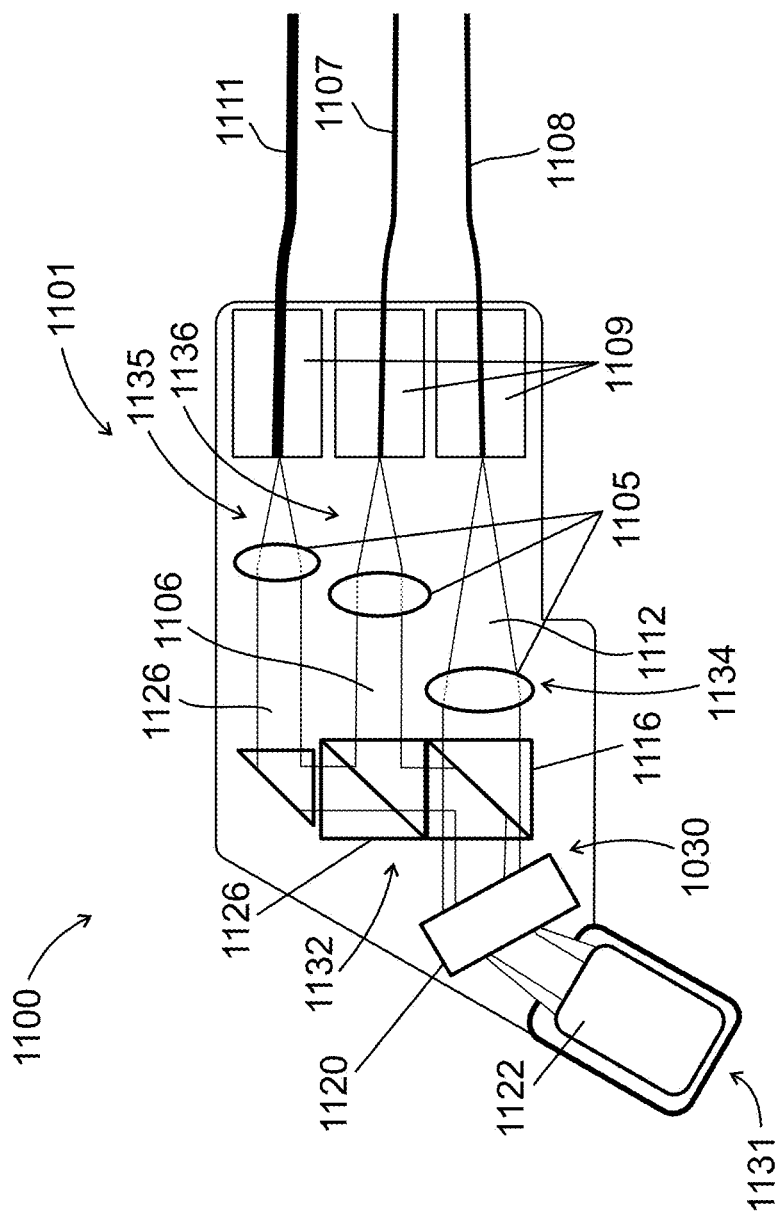
Figure 12:
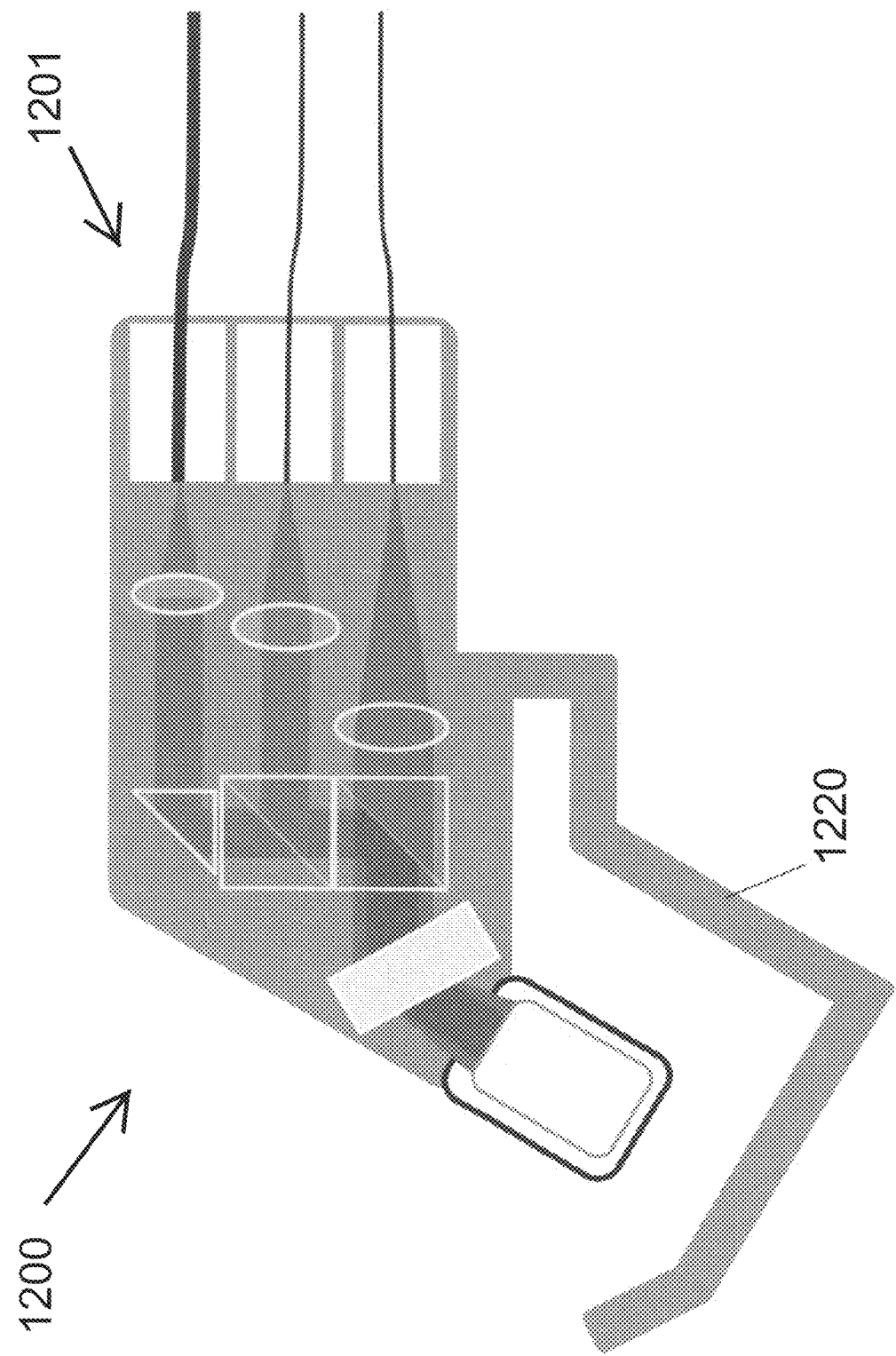
Figure 13:
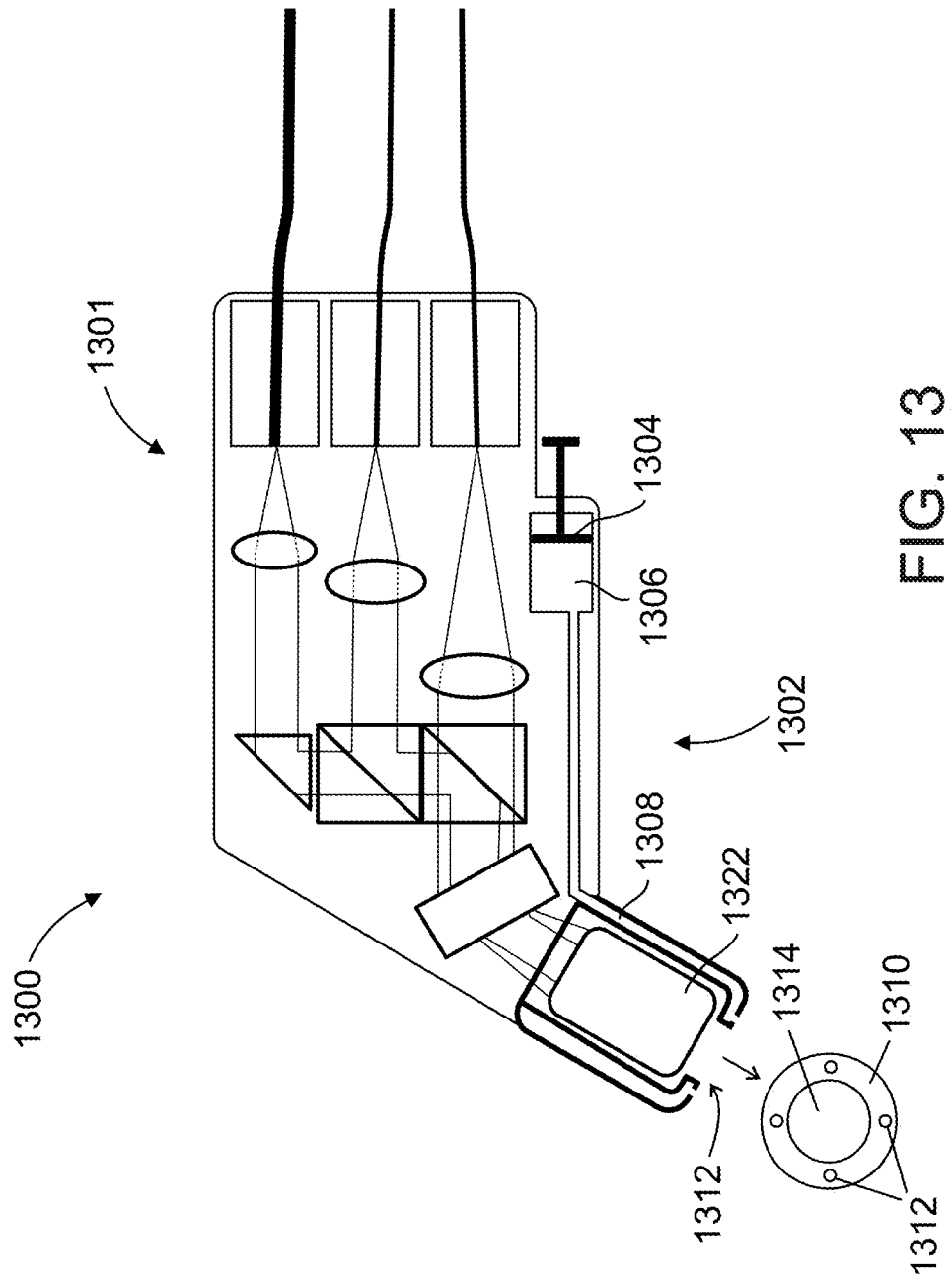
Figure 14:
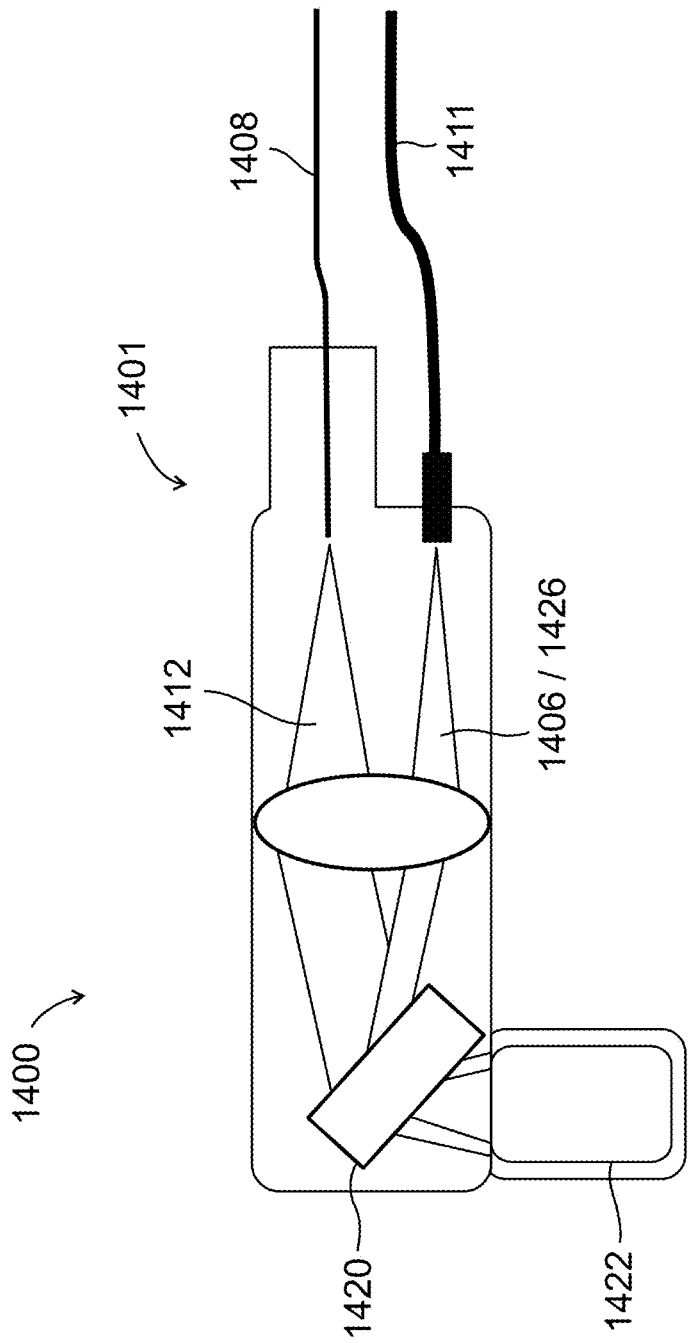
Figure 15:
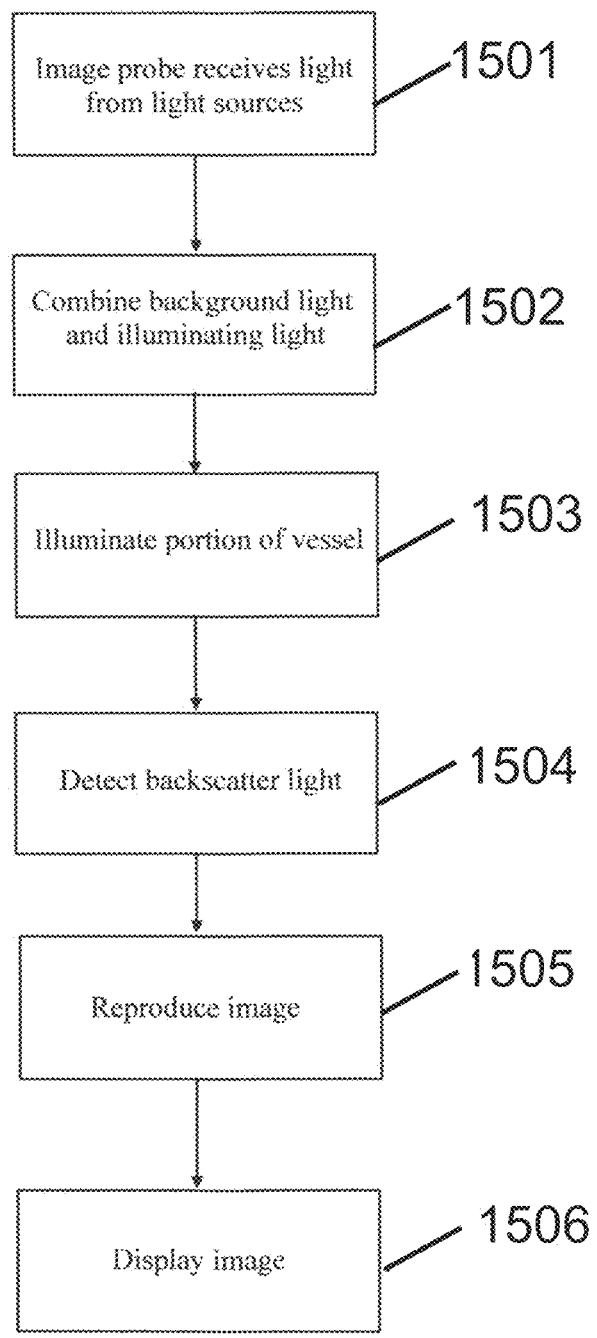
Figure 16:
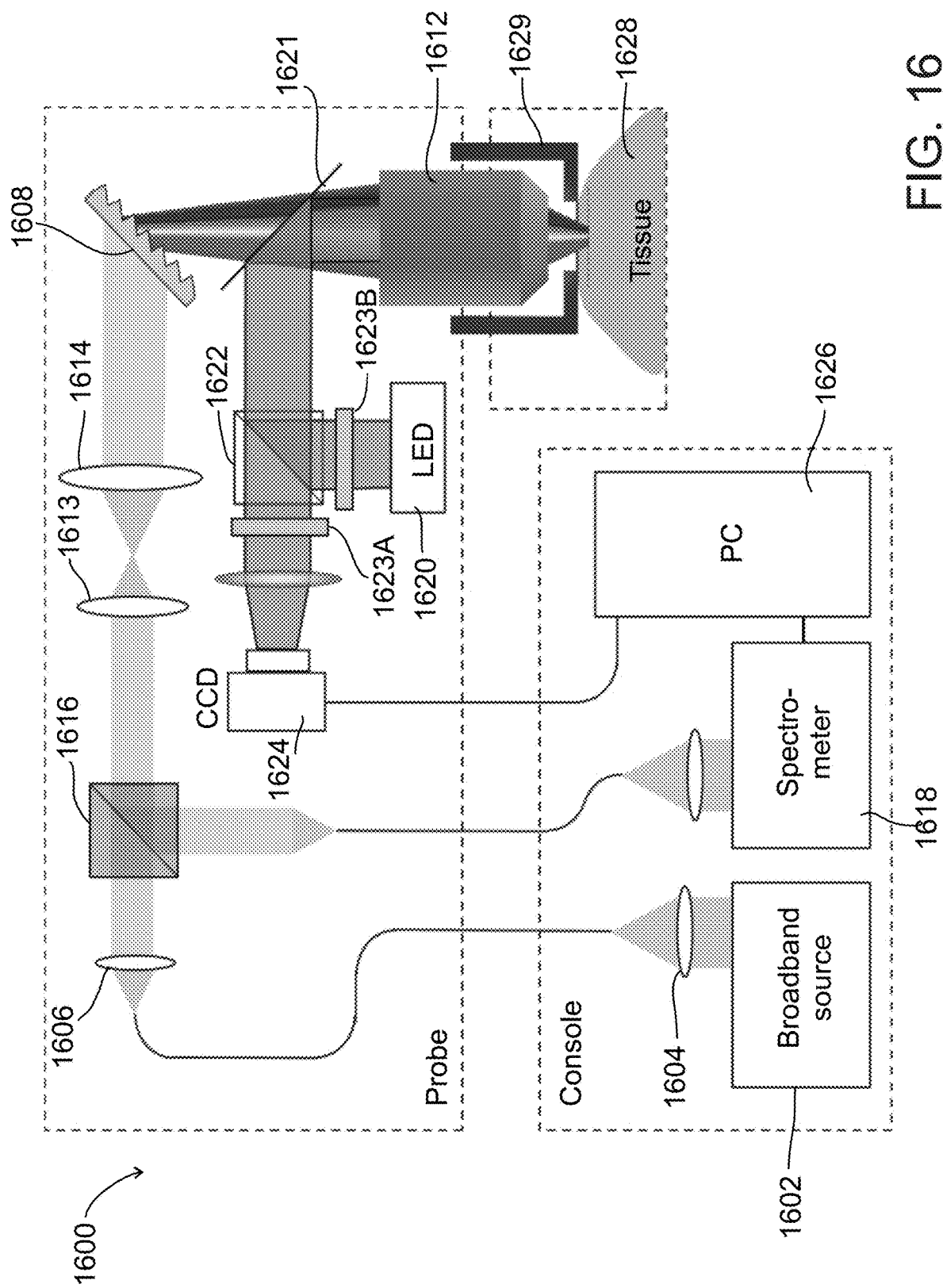
Figure 19A:
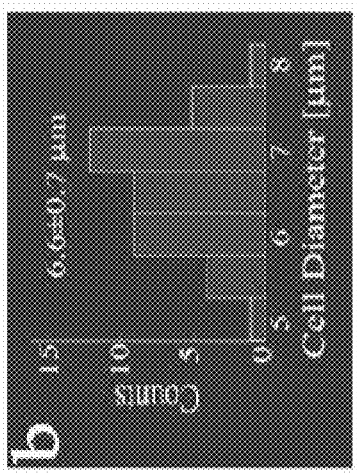
Figure 19B:
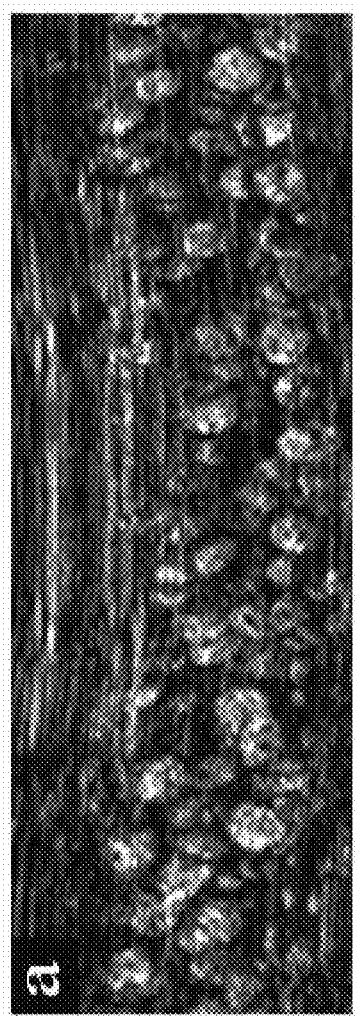
Figure 19C:
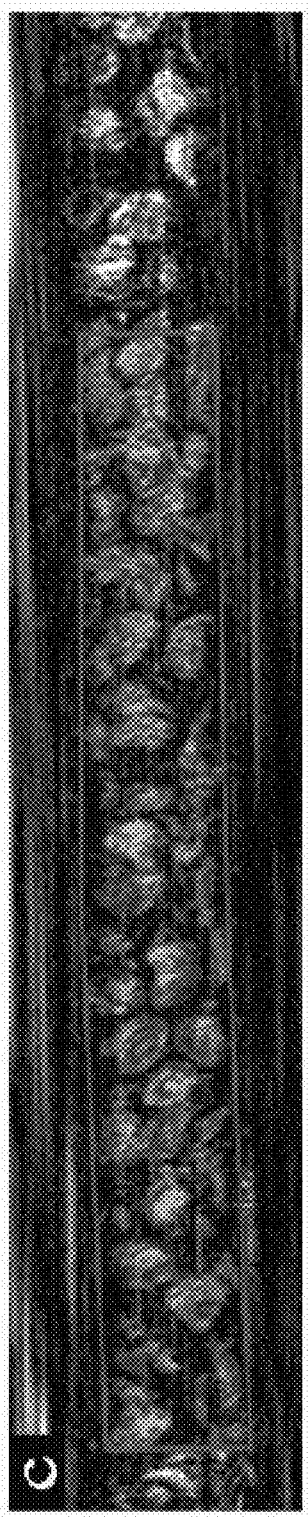
Figure 19D:
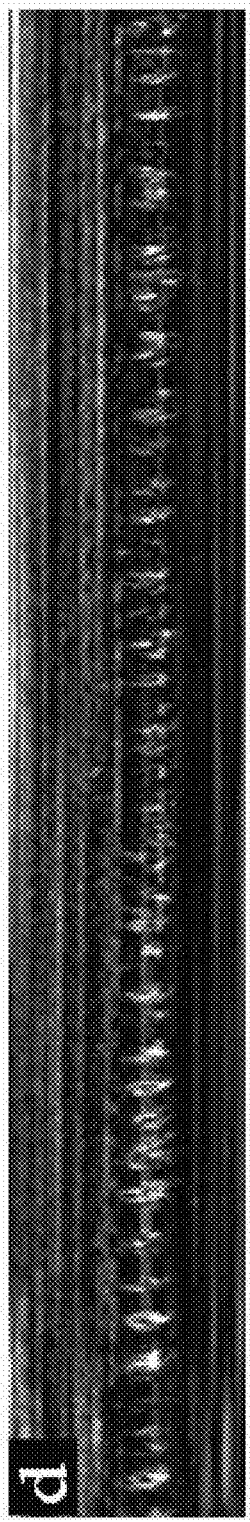
Figure 20A:
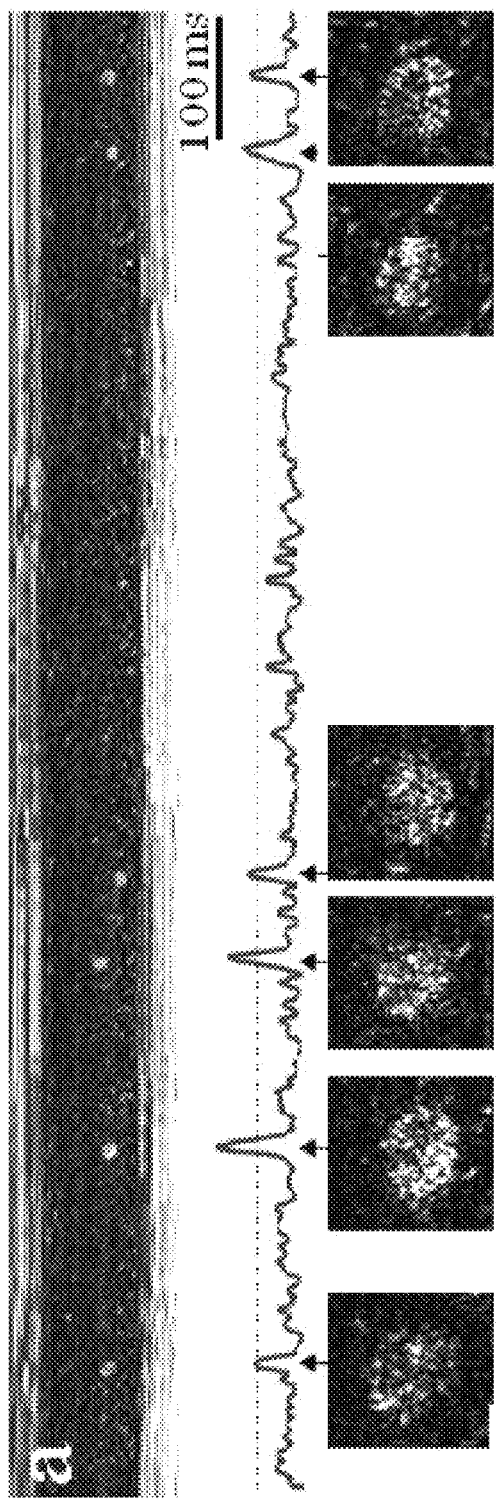
Figure 20C:
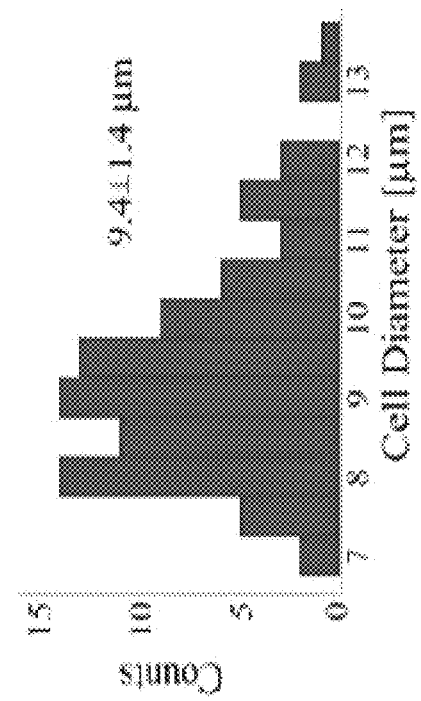
Figure 20B:
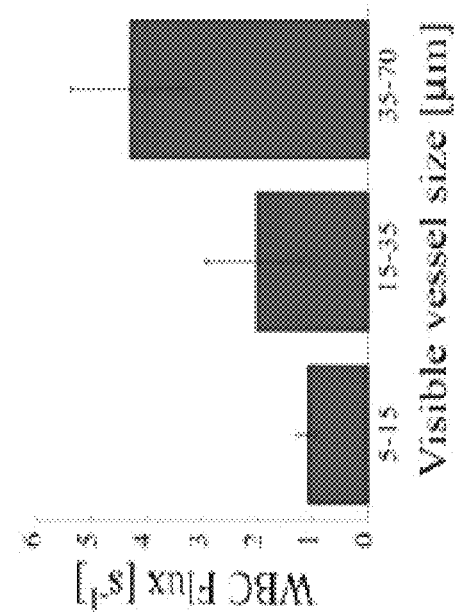
Figure 22:
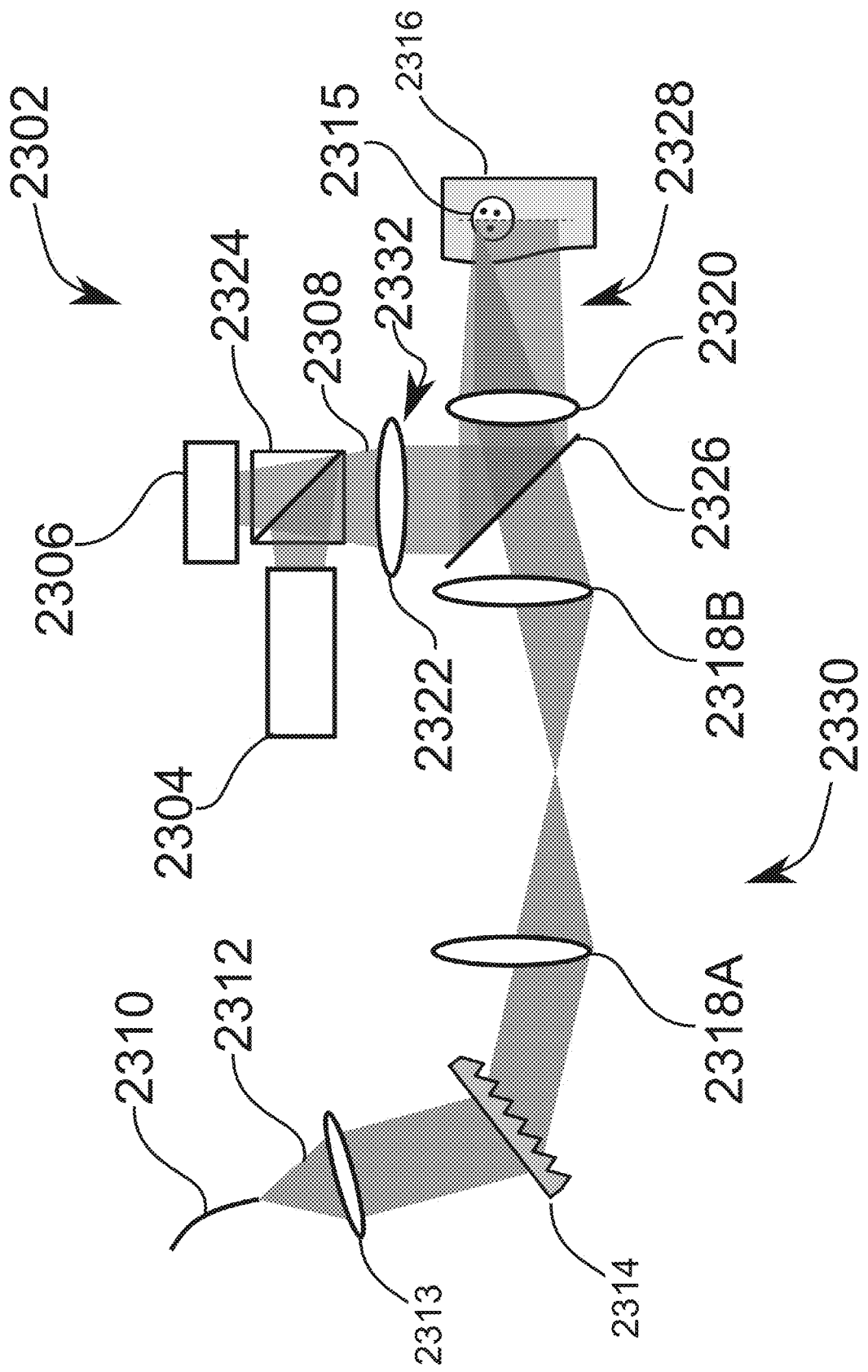

FIG. 1 schematically illustrates a functional block diagram of an exemplary system for imaging a vessel, in accordance with an embodiment of the present invention;

FIG. 2 schematically illustrates a functional block diagram of an exemplary system for imaging a vessel using a broadband light source, in accordance with some embodiments of the present invention;

FIG. 3 schematically illustrates a functional block diagram of an exemplary system for imaging a vessel using a broadband light source and low coherence interferometry, in accordance with some embodiments of the present invention;

FIG. 4 schematically illustrates a functional block diagram of an exemplary system for imaging a vessel using a wavelength-swept light source, in accordance with some embodiments of the present invention;

FIG. 5 schematically illustrates a functional block diagram of an exemplary system for imaging a vessel using a wavelength-swept light source, and single mode and multi-mode optical fibers including a beam splitter, in accordance with some embodiments of the present invention;

FIG. 6 schematically illustrates a functional block diagram of an exemplary system for imaging a vessel using a wavelength-swept light source and single mode and multi-mode optical fibers, in accordance with some embodiments of the present invention;

FIG. 7A schematically illustrates an exemplary single-event histogram from a cytometer, as known in the art;

FIG. 7B schematically illustrates an exemplary cross-sectional image acquired by any exemplary system shown in FIGS. 1-6, in accordance with an embodiment of the present invention;

FIG. 8A illustrates a flow chart of a method for acquiring an image of a particle in a vessel, in accordance with an embodiment of the present invention;

FIG. 8B schematically illustrates a functional block diagram of an exemplary system for imaging a vessel using a wavelength-swept light source and low coherence interferometry, in accordance with some embodiments of the present invention;

FIG. 9 schematically illustrates an imaging probe used in an imaging system for locating a vessel, according to an exemplary embodiment of the invention;

FIG. 10 schematically illustrates an imaging probe used in an imaging system for locating a vessel, according to an exemplary embodiment of the invention;

FIG. 11 schematically illustrates an imaging probe used in an imaging system for locating a vessel, according to an exemplary embodiment of the invention;

FIG. 12 schematically illustrates an imaging probe used in an imaging system for locating a vessel, according to an exemplary embodiment of the invention;

FIG. 13 schematically illustrates an imaging probe used in an imaging system for locating a vessel, according to an exemplary embodiment of the invention;

FIG. 14 schematically illustrates an imaging probe used in an imaging system for locating a vessel, according to an exemplary embodiment of the invention;

FIG. 15 illustrates a flow chart of an exemplary method for locating a vessel, in accordance with an embodiment of the present invention;

FIG. 16 schematically illustrates an experimental setup of a system for locating a vessel, according to some embodiments of the invention;

FIG. 17A illustrates In vitro imaging of flowing blood cells, according to some exemplary embodiments of the invention;

FIG. 17B illustrates In vitro imaging of flowing blood cells, according to some exemplary embodiments of the invention;

FIG. 17C illustrates In vitro imaging of flowing blood cells, according to some exemplary embodiments of the invention;

FIG. 17D illustrates In vitro imaging of flowing blood cells, according to some exemplary embodiments of the invention;

FIG. 18A illustrates In vivo noninvasive imaging of blood flow in a single vessel, according to some exemplary embodiments of the invention;

FIG. 18B illustrates In vivo noninvasive imaging of blood flow in a single vessel, according to some exemplary embodiments of the invention;

FIG. 18C illustrates In vivo noninvasive imaging of blood flow in a single vessel, according to some exemplary embodiments of the invention;

FIG. 18D illustrates In vivo noninvasive imaging of blood flow in a single vessel, according to some exemplary embodiments of the invention;

FIG. 19A illustrates In vivo imaging in micro vessels, according to some exemplary embodiments of the invention;

FIG. 19B illustrates In vivo imaging in micro vessels, according to some exemplary embodiments of the invention;

FIG. 19C illustrates In vivo imaging in micro vessels, according to some exemplary embodiments of the invention;

FIG. 19D illustrates In vivo imaging in micro vessels, according to some exemplary embodiments of the invention;

FIG. 20A illustrates In vivo imaging of white blood cells, WBCs, according to some exemplary embodiments of the invention;

FIG. 20B illustrates In vivo imaging of white blood cells, WBCs, according to some exemplary embodiments of the invention;

FIG. 20C illustrates In vivo imaging of white blood cells, WBCs, according to some exemplary embodiments of the invention;

FIG. 21A illustrates In vivo imaging of white blood cells, WBCs, according to some exemplary embodiments of the invention;

FIG. 21B illustrates In vivo imaging of white blood cells, WBCs, according to some exemplary embodiments of the invention;

FIG. 21C illustrates In vivo imaging of white blood cells, WBCs, according to some exemplary embodiments of the invention;

FIG. 22 schematically illustrates an imaging probe used in an imaging system for locating a vessel, according to an exemplary embodiment of the invention.

DESCRIPTION OF SPECIFIC EMBODIMENTS OF THE INVENTION

The present invention, in some embodiments thereof, relates to imaging devices and, more particularly, but not exclusively, to imaging system and methods for finding capillaries for aiming a sensor at them.

The present invention, in some embodiments thereof, uses the method of particle imaging shown in U.S. application Ser. No. 12/461,558 filed on Aug. 19, 2009 and published as U.S. Patent Application Publication No. 2010/0045778 A1 with publication date Feb. 25, 2010, the contents of which are incorporated by reference as if fully set forth herein. The present invention can also be used with other vessel sensing techniques that sample data about a vessel and/or what is happening in it or near it. The present invention, in some embodiments thereof, may also be used with other vessel sensing techniques and/or to guide the insertion of a biopsy/blood extraction needle. The present invention, in some embodiments thereof, may also be used with other vessel sensing techniques that look at blood analytes.

An aspect of the present invention relates to a method and system for non-invasively locating vessels under a tissue surface by illuminating at least a portion of the vessel using a background light which is more highly absorbed by particles in the vessel relative to the vessel itself, and by detecting a backscattered light from the illuminated vessel. By applying the background light, a contrast background is created by the particles' relatively high absorption of the background light. An image of the backscatter light from the background light may then be processed for determining the location of the vessel. In some embodiments, the vessel is illuminated from a position external to the vessel and may be within a search area which may extend to a substantial depth under the tissue surface. This depth may extend up to 100 μm, or even 200 μm, or more. In some embodiments, a field-of-view of the search area may include a few capillaries, for example, 1, 3, 5, 7, 10, 20, 30, 50 capillaries, or intermediate numbers. In some embodiments, the vessel is within a target area which includes a small portion of the field-of-view of the search area. In an exemplary embodiment of the invention, the target area is used for further sensing and/or treatment. In an exemplary embodiment of the invention, the target area is less than 20%, 10%, 5% or intermediate percentages of the field of view. Optionally or alternatively, the field of view is sized, for example, between 1 and 5 diameters of a blood vessel, in diameter. Optionally or alternatively, the field of view is sized, for example, so that the probability of finding a vessel within it is 50% or 10%, or 5%, or an intermediate probability. Optionally or alternatively, said vessel is an artery or vein of at least 20 μm, 40 μm, 80 μm or intermediate widths. Optionally, only the vessel is in this field-of-view. Optionally, the single vessel is a single capillary. In some embodiments, arriving at the target area may include varying a wavelength of the illumination and/or mechanical intervention. In some embodiments, the background light may cover a square of up to 350 μm by 350 μm. Additionally or alternatively, the background light may cover a square of up to 3 mm by 3 mm. In some embodiments, the vessel can be skin, or a surface of a lumen, for example such as may be found in the naval cavity, a blood vessel, the GI tract, among other body sections.

In some exemplary embodiments, the background light is a wide-field light. Additionally or alternative, the background light is a green light. In some exemplary embodiments, normal blood green light (520 nm wavelength) absorption will range from 6% for a 5 μm diameter vessel to approx. 60% for a 75 μm diameter vessel. Alternatively, the background light is a red light.

In some exemplary embodiments, the background illumination is transmitted together with the spectrally dispersed illuminating light. The illuminating light, which may be a broadband light or a wavelength-swept light, is spectrally dispersed along an axis of the portion of the vessel. Optionally, spectrally dispersing the illuminating light is part of using techniques known in the art such as SEE (spectral encoded endoscopy) and/or SECM (spectrally encoded conformal microscopy). These techniques may be used for viewing the particles inside the vessel for flow cytometry purposes. In some embodiments, transmitting the background light together with the illuminating light allows for locating the vessel and for viewing its particles. In some embodiments, the backscattered light from the illumination is detected and processed for generating an image of the portion of the vessel and/or the particles in the vessel. Additionally or alternatively, the backscattered light from the background is detected and processed for generating an image. Optionally, only the data for producing the image is generated but not the image.

In some exemplary embodiments the reproduced image is a two dimensional (2D) image of the portion of the vessel, and may include a cross-section of the portion of the vessel. Optionally, the portion of the vessel may be automatically indicated on it and/or the indication used for processing, or a user does the indicating on the green image The 2D image may include a cross-section of one or more particles which would be shown as being of a darker or otherwise distinguishable shade compared to other vessel components. A degree of shade intensity may vary between particles or within a particle itself depending on factors such as, for example; the type of particle (red blood cell, white blood cell, leukocytes, granulocytes, etc); the particle's position in the illuminated portion of the vessel; the particle's orientation relative to the direction of illumination and/or direction of flow; particle's size and geometry; among other factors. Additionally or alternatively, a three-dimensional (3D) image may be generated, or a portion thereof.

In some exemplary embodiments, the method and system offer potential advantages over the art as important blood parameters may be non-invasively determined. Some examples of these parameters include hematocrit, and mean corpuscular volume (MCV). The method and system may also be used for establishing new clinical indices derived from the cells' morphology and dynamics within their natural physiological environment. Additionally, the method and system may be used for continuous tracking of hematocrit levels for intra- and post-surgical monitoring of patients for detecting sudden changes in the circulation caused by internal bleeding. Additionally, the method and system may be used for online monitoring of WBC concentration, which may be applied in critical care medicine to detect a rapidly developing inflammatory process. The method and system may also be used for visualizing cellular deformation, aggregation, margination and adhesion, previously studied mainly in animals and which have shown correlation to various pathological states [G. W. Schmid-Schönbein, S. Usami, R. Skalak, and S. Chien, "The interaction of leukocytes and erythrocytes in capillary and post-capillary vessels," Microvascular Research 19, 45-70 (1980); J. J. Bishop, P. R. Nance, A. S. Popel, M. Intaglietta, and P. C. Johnson, "Effect of erythrocyte aggregation on velocity profiles in venules," Am J Physiol Heart Circ Physiol 280, H222-236 (2001)]. The method and system may also be used for assessing patients with hemoglobinopathies such as sickle cell anemia and beta thalassemia, and for providing information on the percentage of sickled and thalassemic cells, respectively. This method may also be used to assess the level of neutrophil-platelet interactions by measuring the degree of aggregation of WBC [K. Konstantopoulos, S. Neelamegham, A. R. Burns, E. Hentzen, G. S. Kansas, K. R. Snapp, E. L. Berg, J. D. Hellums, C. W. Smith, L. V. McIntire, and S. I. Simon, "Venous Levels of Shear Support Neutrophil-Platelet Adhesion and Neutrophil Aggregation in Blood via P-Selectin and β2-Integrin," Circulation 98, 873-882 (1998)]. This method may also be used to screen large populations for anemia and for hematologic malignancies such as leukemia and lymphoma.

In some exemplary embodiments, the method and system may be used in performing in vivo spectrally encoded flow cytometry (SEFC) wherein a plurality of particles in a relatively deep vessel may be substantially counted and optionally examined based on the acquired image. The term "in vivo" as used herein in this disclosure, refers to inside a body, for example the body of a patient. Optionally, performing of SEFC may be made ex vivo, The terms "ex vivo", and "in vitro" as used herein in this disclosure, refers to outside of the body, for example, as in vessels and/or organs externally connected to the body (optionally artificial), as in cultures, as in samples used in hydrodynamic-based flow cytometry, as in blood of a patient undergoing extracorporeal therapy such as hemodialysis or apheresis, and/or as in blood samples extracted from the body. The system may determine a number of particles of different types in the vessel, including in a single capillary, and optionally, their location, speed of flow, size, length, shape, orientation, color, or brightness, or any combination thereof. These particles may include, but not be limited to, red blood cells, white blood cells, platelets, blood cell aggregates, parasites, circulating tumor cells, blood clots, gas bubbles, virus, amoeba, germ cells, bacteria, toxins, medicines, stained beads, nano-particles, DNA, RNA, among other microscopic particles adapted to relatively absorb the background light compared to surround components. The term "number" refers to a discrete quantity, and may optionally be a statistic or a relative number.

In an exemplary embodiment of the present invention, the system comprises a light source for generating the background light; an imaging probe for illuminating the portion of the vessel and for capturing the backscattered light from the illuminated vessel; a detection unit for detecting the backscattered light; a processing unit for reproducing the image of the illuminated portion of the vessel; and a display for displaying the 2D cross-sectional image of the illuminated vessel. Additionally or alternatively, the display displays the 3D image or a portion thereof. The processing unit additionally performs all image and data analysis, including determination of average flow velocity of the particles in the vessel and concentration of particles in the vessel. In some embodiments, the system includes a light source for generating the illuminating light. Optionally, the images displayed include the particles or portions thereof.

In some exemplary embodiments, the imaging probe is of a relatively small size. Optionally, the imaging probe is adapted to be held in a single hand by a user. In one embodiment, the probe is 11 cm by 5.5 cm by 2.5 cm. In another embodiment, the probe is 6 cm by 4 cm by 1 cm. In an endoscopic example, the probe may have a diameter of, for example, less than 2 cm, 1 cm, 0.8 cm or intermediate diameters. Optionally, the imaging probe does not include any moving mechanical parts. Alternatively, moving mechanical parts are restricted to those required for focusing, for example, by mechanically moving a focusing lens relative to a cap on the probe. Alternatively, mechanically moving parts are used to scan the tissue for a capillary. Alternatively, focusing may be performed by pressing the probe against the tissue. In some embodiments, the imaging probe may be an endoscopic probe. Alternatively, imaging probe may be a catheter scope.

In some exemplary embodiments, the background light source is housed in the imaging probe. Optionally, the background light source includes a LED. Optionally, the LED is operated by a battery. Additionally or alternatively, the probe houses the detection unit, which may include a CMOS camera, a CCD camera, or any other image acquisition means known in the art and suitable for acquiring an image of the backscattered light against the contrast background. Optionally, the CCD transmits the acquired image to the processing unit wirelessly. Additionally or alternatively, the image probe houses the processing unit. Optionally, the processing unit transmits the acquired image to the display wirelessly.

In some exemplary embodiments, the imaging probe is connected to the illuminating light through a single-mode optical fiber. Optionally, the connection of the imaging probe to the background light source is through a multi-mode optical fiber. In some embodiments, the connection of the imaging probe to the detection unit is through a multi-mode optical fiber.

In some exemplary embodiments, the imaging probe includes a fixation mechanism for minimizing relative motion between the imaging probe and the tissue without user control, thereby permitting longer imaging periods. In some embodiments, the fixation mechanism includes a low pressure vacuum suction for fixing the tissue in place. Alternatively, the fixation mechanism includes an adhesive which temporarily attaches the probe to the tissue.

In some embodiments of the present invention, the illumination light is coupled to a fiber coupler on the imaging probe where it is also collimated, diffracted and focused onto a transverse spectral line on the portion of the vessel. Backscattered light that is scattered back from the transverse spectral line is collected by an objective lens in the imaging probe, where it is coupled back into the fiber, and then measured by a fast spectrometer. This optical configuration permits a single-shot line imaging of the particles flowing across the transverse spectral line, and allows fast confocal imaging across the vessel without any scanning mechanism.

In some embodiments of the present invention, low coherence interferometry is used to achieve depth information. By adding the reference arm, emitted light interferes with a reference light, which allows determining an axial location (for example along a z-axis or an x-axis, a y-axis, or any non-principal axis) of the illuminated particle, as well as increase sensitivity and speed of the system. Using the coherence gate allows using a lower numerical-aperture lens which simplifies the system and provides larger depth range.

An aspect of some embodiments of the present invention relates to an imaging probe which is configured to be a beam combiner for providing light from different sources a common aperture for illumination, and a beam splitter for providing backscatter light destined to different receivers the common aperture for reception. The imaging probe includes a beam combiner/splitter connected on one side through a common optical channel to the aperture, and on the other side to a plurality of optical channels which lead to light sources and/or light receivers. All light entering and leaving through the aperture pass through the common optical channel. In some embodiments of the present invention, the plurality of optical channels includes separate illumination and backscatter channels. In some embodiments, the combiner/splitter is a same optical component.

Alternatively, they are separate components (combiner and splitter). A single-mode fiber is optionally used for the illuminating light and background light while a multimode fiber with larger core is optionally used for the background light and to collect the backscattered light after passing through the combiner/splitter. This technique potentially improves one or more of signal efficiency, depth of field, speckle noise and reduces undesired back reflections.

For purposes of better understanding some embodiments of the present invention, as illustrated in FIGS. 9-22 of the drawings, reference will first be made to FIGS. 1-8A incorporated from the related application, and FIG. 8B.

FIGS. 1-8 relate to a system and method for performing flow cytometry including a technique of creating a transverse spectrally encoded line across a vessel and imaging a reflectance of particles as they flow across the line. A 2D image of the particles is then formed, one axis is encoded by the wavelength of the reflectance, and a second axis is encoded by time.

FIGS. 9-22 relate to a system and method for locating a vessel, and may also use the technique of creating a transverse spectrally encoded line across the vessel described in the system/method of FIGS. 1-8. Furthermore, a 2D image of the vessel and particles formed has one axis encoded by time as per the system/method of FIGS. 1-8.

Accordingly, it has been decided to first describe the FIGS. 1-8. Nevertheless, FIGS. 1-8 show only one example of sensing, whereas the system and method per FIGS. 9-22 may use other types of sensing techniques, including light as well as ultrasound. For example, a type of sensing technique is photo-acoustic detection. In some embodiments, the sensors may be 1-dimensional, 2-dimensional or 3-dimensional sensors, and may be placed at multiple points along the capillary. Optionally, the sensors are aligned according to capillary axis, but may not apply to all sensors.

Referring now to the drawings, FIG. 1 schematically illustrates a functional block diagram of an exemplary system 100 for imaging a vessel 116, in accordance with an embodiment of the present invention. System 100 includes a light source 102, an imaging probe 106 including optical elements 107, a detection unit 110, a processor unit 112, and a display unit 114.

According to an embodiment of the present invention, system 100 acquires an image of one or more of a same type, or optionally a different type, of particles flowing in vessel 116, for example as shown by particles 120, 122 and 124 in body fluid 118, by laterally statically illuminating a portion of the vessel with an illuminating light 108 produced by light source 102, and detecting an emitted light (not shown) produced by the particles. Optionally, system 100 acquires an image of vessel 116. Optionally, system 100 includes a use of SEE. Optionally, system 100 includes a use of SECM. Particles 120-124 may include red blood cells, white blood cells, virus cells, amoeba, germ cells, bacteria, toxins, medicines, nano-particles, DNA, RNA, among other microscopic particle visible in lights. Vessel 116 may include veins, arteries, venules, arterioles, capillaries, artificial vessels, microfluidic systems, lymph, urinary tract, and other ducts internal, or optionally external, to the body and which may carry body fluids and particles.

Illuminating of the portion of vessel 116 may be performed by imaging probe 106, which may include for example, an endoscope, optionally a catheter. Illuminating light 108, which may include a broadband illuminating light or a wavelength-swept illuminating light, is guided from light source 102 to imaging probe 106 by an optical waveguide 104, which may include, for example a single optical fiber, or optionally, multiple optical fibers. Optical fiber 104 may be a single-mode optical fiber or optionally, a multi-mode optical fiber. Optionally, optical waveguide 104 may comprise reflecting mirrors and/or other optical elements suitable for directing light. Illuminating light 108 is spectrally dispersed along an x-axis and/or a y-axis of vessel 116 by optical elements 107 in imaging probe 106 which include a diffraction grating. Optionally, illuminating light 108 is spectrally dispersed along a z-axis. Illumination light 108 may comprise a wavelength in the range from 600 nm-1.3 μm. A potential advantage of using light of greater wavelength is a reduction in scattering and an increase in depth range.

Imaging probe 106 additionally collects the emitted light from particles 120-124, and optionally from vessel 116, and optically converts the emitted light using optical elements 107 for guiding to detection unit 110. The emitted light may include, but not be limited to, fluorescence, second harmonic generation, third harmonic generation, luminescence, coherent anti-Stokes Raman scattering, Raman scattering, multiphoton fluorescence, phosphorescence, or any combination thereof. Optionally, capturing of emitted light is done by a second light capturing probe. Guiding of the emitted light from imaging probe 106 to detection unit 110 is done through optical fiber 104. Optionally, guiding is done through a second optical fiber, which may be a single-mode optical fiber, or optionally, a multi-mode optical fiber.

Emitted light captured by imaging probe 106 is detected by detection unit 110, and an output associated with a measure of a spectrum of the emitted light is generated for processing by processing unit 112. Detection unit 110 is selected according to the emitted light to be detected, and may include a spectrometer for measuring a distinct spectral band in the emitted light, a CCD camera for capturing a single shot of the emitted light, or a single detector for measuring a discrete wavelength of the emitted light, or any combination thereof. The emitted light may also be subject to low coherence interferometry with a reference light in reference arm 115 so that an axial (z-axis) location of particles 120-124 may be determined and used to obtain a 3D image. Optionally, an axial component of a speed of particles 120-124 is determined. Optionally, Doppler imaging is used to acquire the axial component of the speed of the particle.

According to an embodiment of the present invention, processing unit 112 processes the output from detection unit 110 and reproduces the acquired image of particles 120-124, and optionally vessel 116 and/or body fluid 118, for display on display unit 114. The reproduced image may be a cross-sectional 2D image along an x-axis and a y-axis, or optionally a 3D image (depth along a z-axis), of particles 120-124. The reproduced image may additionally comprise a cross-sectional 2D image, or optionally a 3D image, of the portion of vessel 116 and/or body fluid 118. Optionally, the reproduced image may include information related to the velocity of the particles.

According to an embodiment of the present invention, system 100 performs in vivo, and optionally ex vivo, flow cytometry. Based on the output of detection unit 110, processing unit 112 may simultaneously count, and optionally examine, particle 120-124, and may compute a number of particles of different types in vessel 116, and optionally, their location, speed of flow, length, shape, color, or brightness, or any combination thereof. The results of the computation may be displayed in display unit 114. Optionally, the results may be stored in magnetic media or other data storage means, printed, displayed by means other than display unit 114, or any combination thereof.

Reference is made to FIG. 2 which schematically illustrates a functional block diagram of an exemplary system 200 for imaging a vessel 216 using a broadband light source 202, in accordance with some embodiments of the present invention. Vessel 216 is shown under tissue 217, and comprises body fluid 218 and particles 220, 222 and 224, which may be similar to that shown in FIG. 1 at 116, 118, 120, 122, and 124.

System 200, which may be similar to that shown in FIG. 1 at 100, comprises broadband light source 202 which may include a super-luminescent diode array; an optical waveguide 204 which may include an optical fiber; an imaging probe 206 including optical elements comprising a diffraction grating 207A for diffracting illuminating light 208, a collimator 207B for collimating the illuminating light, and a high NA focusing lens 207C for focusing the illuminating light; a spectrometer 210 including a CCD camera 210C, a collimator 210A for collimating an emitted light 209 and a diffraction grating 210B for diffracting the emitted light; a processing unit 212; and a display unit 214. Broadband light source 202; optical waveguide 204; imaging probe 206 including diffraction grating 207A, collimator 207B, and lens 207C; CCD camera 210 with collimator 210A and diffraction grating 210B; processing unit 212; and display unit 214; may be similar to that shown in FIG. 1 at 102, 104, 106 including 107, 110, 112, and 114.

According to some embodiments of the present invention, single-shot line imaging, and fast confocal imaging across vessel 216 is performed, without any scanning mechanism. Broad bandwidth illuminating light from light source 202 is coupled to optical fiber 204, collimated, spectrally diffracted and focused onto a transverse line (focal line) within a flow of body fluid 218 and particles 220-224 inside vessel 216, where each resolvable point on the line contains a single wavelength (each point is illuminated by a distinct spectral band). Emitted light 209 from each line is collected by imaging probe 206, coupled back into fiber 204, and measured by fast spectrometer 210. An output of spectrometer 210 is processed by processing unit 212 and displayed on display unit 214.

FIG. 3 schematically illustrates a functional block diagram of an exemplary system 300 for imaging a vessel 316 using a broadband light source 302 and a reference arm 315, in accordance with some embodiments of the present invention. Vessel 316 is shown under tissue 317, and comprises body fluid 318 and particles 320, 322 and 324, which may be similar to that shown in FIG. 1 at 116, 118, 120, 122, and 124.

System 300, which may be similar to that shown in FIG. 1 at 100, comprises a broadband light source 302 which may include a super-luminescent diode array; an optical waveguide 304 which may include an optical fiber; an imaging probe 306 including optical elements comprising a diffraction grating 307A for diffracting illuminating light 308, a collimator 307B for collimating the illuminating light, and a focusing lens 307C for focusing the illuminating light; a spectrometer 310; a processing unit 312; a display unit 314; and reference arm 315. Broadband light source 302; optical waveguide 304; imaging probe 306 including diffraction grating 307A, collimator 307B, and lens 307C; spectrometer 310; processing unit 312; display unit 314; and reference arm 315; may be similar to that shown in FIG. 1 at 102, 104, 106 including 107, 110,112, 114, and 115.

According to some embodiments of the present invention, low coherence interferometry in the range of 1 μm-10 mm, inclusively, is used to achieve depth information (3D topological information). The interferometry may be in the time domain and/or spectral domain. Reference arm 315, which may be included in a single-mode Michelson interferometer, creates interference between emitted light (not shown) from illuminated particles 320-324, and optionally from vessel 316 and/or body fluid 318, and a reference light, which allows for processing unit 312 determination of an axial (z-axis) location of the particles. Optionally, reference arm 315 may be included in a multimode Michelson interferometer. Optionally, reference arm 315 may be included in any other type of interferometer suitable for creating the interference. Optionally, system 300 sensitivity is increased. Optionally, system 300 imaging speed is increased. Optionally, a lower numerical aperture lens 307C may be used, reducing a complexity of system 300 and increasing a depth range. Optionally, Doppler imaging is used to determine the axial component of the velocity of the particle.

Broad bandwidth illuminating light from light source 302 is coupled to optical fiber 304, collimated, diffracted and focused within a flow of body fluid 318 and particles 320-324 inside vessel 316, where each resolvable point on the line contains a single wavelength. Emitted light (not shown) is collected by imaging probe 306, coupled back into fiber 304 and into reference arm 315, and measured by spectrometer 310. An output of spectrometer 310 is processed by processing unit 312 and displayed on display unit 314, and may include a 3D image or particles 320-324, vessel 316, or body fluid 318, or any combination thereof.

FIG. 4 schematically illustrates a functional block diagram of an exemplary system 400 for imaging a vessel 416 using a wavelength-swept light source 402, in accordance with some embodiments of the present invention. Vessel 416 is shown under tissue 417, and comprises body fluid 418 and particles 420, 422 and 424, which may be similar to that shown in FIG. 1 at 116, 118, 120, 122, and 124.

System 400, which may be similar to that shown in FIG. 1 at 100, comprises a wavelength-swept light source 402 for producing illumination light of varying discrete wavelengths; an optical waveguide 404 which may include an optical fiber; an imaging probe 406 including optical elements comprising a diffraction grating 407A for diffracting illuminating light 408, a collimator 407B for collimating the illuminating light, and a focusing lens 407C for focusing the illuminating light; a detection unit 410 which may include a single-element photo detector; a processing unit 412; and a display unit 414. Wavelength-swept light source 402; optical waveguide 404; imaging probe 406 including diffraction grating 407A, collimator 407B, and lens 407C; photo detector 410; processing unit 412; and display unit 414; may be similar to that shown in FIG. 1 at 102, 104, 106 including 107, 110, 112, and 114.

According to some embodiments of the present invention, confocal imaging of a diffracted wavelength-swept illumination light 408 is done by relatively rapidly changing the wavelength of the light such that every point along a focal line in vessel 416 is illuminated (encoded) with a different wavelength while scanned one point at a time. By using point-by-point illumination, a need for spectral detection of the emitted light is eliminated and detection may be performed by a single-element photo detector 410.

Wavelength-swept illuminating light from light source 402 is coupled to optical fiber 404, collimated, diffracted and focused point-by-point within a flow of body fluid 418 and particles 420-424 inside vessel 416 such that each point is illuminated one-at-a-time by light of a single wavelength (by scanning one at a time). Emitted light (not shown) from each point in each line is collected one-by-one by imaging probe 406, coupled back into fiber 404, and measured by single-element photo detector 410. An output of photo detector 410 is processed by processing unit 412 and displayed on display unit 414.

FIG. 5 schematically illustrates a functional block diagram of an exemplary system 500 for imaging a vessel (not shown) using a wavelength-swept light source 502, and a single-mode optical waveguide 504A and a multi-mode optical waveguide 504B for guiding an illumination light 508A and an emitting light 508B, respectively, in accordance with some embodiments of the present invention.

System 500, which may be similar to that shown in FIG. 1 at 100, comprises wavelength-swept light source 502 for producing illumination light of varying discrete wavelengths; single-mode optical waveguide 504A and multi-mode optical waveguide 504B which may each include an optical fiber; an imaging probe 506 including optical elements comprising a diffraction grating 507A for diffracting illuminating light 508A, a collimator 507B for collimating the illuminating light, a focusing lens 507C for focusing the illuminating light, a coupler 507D for coupling emitting light 508B to optical fiber 504B, and a beam splitter 507E for splitting the emitted light; a detection unit 510 which may be a single-element photo detector; a processing unit 512; and a display unit 514. Optionally, beam splitter 507E may be a dichroic mirror for fluorescence detection. Wavelength-swept light source 502; optical waveguides 504A and 504B; imaging probe 506 including diffraction grating 507A, collimator 507B, lens 507C, coupler 507D, and beam splitter 507E; photo detector 510, processing unit 512, and display unit 514, may be similar to that shown in FIG. 1 at 102, 104, 106 including 107, 110, 112, and 114.

System 500 is configured such that a proximal unit 501 includes light source 502, photo detector 510, processing unit 512, and display unit 514 with imaging probe (distal unit) 506 distally located. Connection of imaging probe 506 to proximal unit 501 is through optical fibers 504A and 504B.

According to some embodiments of the present invention, single-mode optical fiber 504A is used for high-resolution illumination while multi-mode optical fiber 504B with a larger core collects a backscattered/fluorescence emitted light 508B after passing through beam splitter 507E, optionally the dichroic mirror. Wavelength-swept illuminating light from light source 502 is coupled to optical fiber 504A, collimated, diffracted and focused onto a transverse line (focal line) in a vessel (not shown), where each resolvable point on the line contains a single wavelength (each point is illuminated by one by one by scanning one at a time). Emitted light (not shown) from each point in each line is collected one-by-one by imaging probe 506, split into separate beams by beam splitter 507E, optionally the dichroic mirror, and coupled into multi-mode optical fiber 504B. The beams are measured by single-element photo detector 510 and an output of the photo detector is processed by processing unit 512 and displayed on display unit 514.

FIG. 6 schematically illustrates a functional block diagram of an exemplary system 600 for imaging a vessel (not shown) using a wavelength-swept light source 602, and a single-mode optical waveguide 604A and a multi-mode optical waveguide 604B for guiding an illumination light 608A and an emitting light 608B, respectively, in accordance with some embodiments of the present invention.

According to some embodiments of the present invention, spatially separating between fluorescence in the illuminated particle and/or illuminated vessel, and an illuminating light 608A, allows for using system 500 shown in FIG. 5 without a beam splitter. Therefore, system 600 may be similar to system 500 with the exception that the system does not include beam splitter 507E shown in FIG. 5.

System 600 comprises wavelength-swept light source 602 for producing illumination light of varying discrete wavelengths; single-mode optical waveguide 604A and multi-mode optical waveguide 604B which may each include an optical fiber; an imaging probe 606 including optical elements comprising a diffraction grating 607A for diffracting illuminating light 608A, a collimator 607B for collimating the illuminating light, a focusing lens 607C for focusing the illuminating light, and a coupler 607D for coupling emitting light 608B to optical fiber 604B; a detection unit 610 which may be a single-element photo detector; a processing unit 612; and a display unit 614. Wavelength-swept light source 602; optical waveguides 604A and 604B; imaging probe 606 including diffraction grating 607A, collimator 607B, lens 607C, and coupler 607D; photo detector 610, processing unit 612, and display unit 614, may be similar to that shown in FIG. 5 at 502; 504A; 504B; 506 including 507A, 507B, 507C, and 507D; 510, 512, and 514.

System 600 is configured such that a proximal unit 601 includes light source 602, photo detector 610, processing unit 612, and display unit 614 with imaging probe (distal unit) 606 distally located. Connection of imaging probe 606 to proximal unit 601 is through optical fibers 604A and 604B.

FIG. 8B schematically illustrates a functional block diagram of an exemplary system 2200 for spread-spectrum interferometric imaging of particle flow. Embodiments of method and construction for spread-spectrum interferometric imaging of particle flow are also shown in "High-speed interferometric spectrally encoded flow cytometry" by L. Golan et al, Optics Letters 37 No. 24, Dec. 15, 2012. In an exemplary embodiment, the system includes an illumination light source 2202 capable of producing a plurality of relatively limited wavelength ranges in rapidly changing ordered or non-ordered succession throughout a wider sweep range. In some embodiments of the present invention, said illumination light source may be a wavelength-swept light source. The system further comprises interferometric apparatus 2215 in accordance with some embodiments of the present invention. The interferometric apparatus 2215 may include the reference arm of a single-mode Michelson interferometer or other interferometer type. The interferometry the interferometric apparatus helps perform may be low coherence interferometry operating within a coherence range of 1 μm-10 mm, inclusively; for example, in the range of 1 μm up to 10 μm, or up to 100 μm.

During imaging, the output wavelength range of the illumination light source 2202 is changed relatively rapidly throughout its sweep range, which in one embodiment may be 1005-1115 nm. In other embodiments, it may be a range with a center wavelength between 800 and 1300 nm inclusive, and a bandwidth between 10 and 300 nm inclusive. In some embodiments of the invention, the choice of the range is made to reduce or control light scattering, and/or to increase or reduce absorption by one or more components of the target vessel, its environs, or the particles within it; for example, for an advantage in light penetration to the target, or in extracting spectral information about the particles.

In one embodiment, scanning through said sweep range occurs at 100 KHz. In other embodiments, said sweep range is above 10 KHz. In an exemplary embodiment of the invention, a light source 2202 is coupled to optical waveguide 2204, which may be an optical fiber, through which the illumination light 2208 enters the probe 2206.

In some embodiments of the invention, the illumination light is collimated at collimator 2207B, and directed toward dispersing element 2207A, which may be a diffraction grating, that spectrally disperses said light. The angle at which light leaves the dispersing element 2207A varies with wavelength, such that points along an axial line in vessel 2216, to which the light is focused to by focusing lens 2207C, are illuminated (encoded) with different wavelengths, one wavelength-determined axial location at a time.

Light returning or emitted from illuminated particles 2220-2224, and optionally from vessel 2216 and/or body fluid 2218, is coupled back into optical waveguide 2204. In an exemplary embodiment of the invention, an interferometric apparatus 2215 creates interference between the returned or emitted light (not shown) and a reference light. In this exemplary embodiment, the light received at the detection unit, 2210, may thus encode, by its intensity and time of arrival, the position and relative reflectance or other light-interaction properties of tissue, fluid, and particles along the illuminated axis.

In some embodiments of the invention, conversion of this encoded information to an image occurs in the processing unit 2212. Demodulation may be by means of a discrete Hilbert transform, a Fourier transform, or another demodulating transformation. From the demodulated data, a line image may be formed from which the axial location of the particles may be determined. By placing line scans in sequential apposition, a two-dimensional (2D) image may be formed for display by display unit 2214. Further particle, tissue, and fluid measurements, including determinations of optical properties, may be performed on the original or on the demodulated data.

Previous reference has been made to the axial location of particles and other components of the vessel or its environs, which may be along a z-axis, pointing orthogonally away from the imaging probe, an x-axis, running substantially perpendicular to the length of a vessel, a y-axis, running substantially parallel to the length of a vessel, or any non-principal axis. The axial location may also be considered with respect to the axis of spectral dispersion, which may be curved or discontinuous in space. The wavelengths which fall on or within an illuminated vessel are not necessarily all of those which an embodiment of the system produces. Some wavelength information regarding the vessel may in this case be unobtainable without further steps or elements. This problem may be addressed in an exemplary embodiment by changing the positioning of optical elements to focus the line of illumination to be smaller or larger, and in another exemplary embodiment by changing the position of optical elements to rotate the line relative to the positioning of the probe. In some embodiments, within any limits that may be imposed by the vessel's situation and the probe's size and construction, the line may also be rotated by changing the positioning of the probe itself. By one of these or similar methods, the illumination of the vessel 2216 may be aligned along an at least partially longitudinal axis of the vessel, in this and other embodiments. This brings more of the spectral range of the illuminating light to bear upon targets within the vessel, providing an advantage for determining the optical property of color (spectrum) by the processing unit 2212.

In this and other embodiments, where at least one set of imaged particles, such as red blood cells, is substantially the same in color (spectrum) properties within the imaged region, the partial spectral information available for each particle (based on the relative return of light across the range of illuminating wavelengths) may be combined by processing unit 2212, for example by time-averaging at a plurality of spectral ranges, to make a combined assessment of the spectral properties of the set. In the case of red blood cells, for example, spectral properties depend on a level of oxygen saturation.

By means of the interferometric imaging embodiment just described for the system 2200, sensitivity and imaging speed are increased over some other embodiments. This may permit the determination, for example, of faster flow rates (appropriate to small veins and arteries) up to about 10 mm/s, where different embodiments, such as some that rely on a broad-band light, determine flow rates (appropriate chiefly to capillaries) only up to about 1.5 mm/s. Optionally, Doppler measurement is used to determine the axial component of the velocity of the particle.

Reference is made to FIG. 7A which schematically illustrates an exemplary single-event histogram from a cytometer, as known in the art, and to FIG. 7B which schematically illustrates an exemplary cross-sectional image along an x-axis and a y-axis of the of a vessel acquired by any one of system 100-600 shown in FIGS. 1-6, in accordance with an embodiment of the present invention. The single-event histogram shown in FIG. 7A is based on a use of a single laser beam aimed at a hydrodynamically-focused stream of fluid for counting particles one-by-one. From the cross-sectional image shown in FIG. 7B, additional information on particles aside from their number, such as for example, type, size, shape, location in the vessel, color, brightness, and the like, may be readily obtained. The additional information may be used to increase the speed of measurement by increasing the flow rate, its accuracy, and for the implementation of new cell collection systems that may use this information for more efficient and accurate cell sorting.

Reference is made to FIG. 8A which illustrates a flow chart of an exemplary method for acquiring an image of a particle in a vessel, in accordance with an embodiment of the present invention. Reference is also made to FIG. 1. It should be evident to a person skilled in the art that the exemplary method described herein may be implemented in other ways, forms, and/or manners, and is therefore not intended to be limiting to the method described.

At 801, illumination light 108 is produced by light source 102 and sent over optical waveguide 104 to imaging probe 106 which may include an endoscope or a catheter. Illumination light 108 may be a broadband light or a wavelength-swept light. Optical waveguide 104 may be a single-mode optical fiber. Optionally, waveguide 104 may be a multi-mode optical fiber.

At 802, illumination light 108 is received by imaging probe 106 where the light is collimated by a collimator and spectrally diffracted by a diffracted grating in optical element 107. Optionally, illumination light 108 is not collimated.

At 803, a portion of vessel 116 is illuminated by illumination light 108, the light spectrally dispersed along the x-axis of the vessel.

At 804, particles 120-124, and optionally illuminated vessel 116 and/or body fluids 118, produce emitted light responsive to being illuminated by illumination light 108. Imaging probe 106 collects (captures) the emitted light which is optically processed by optical element 107 for sending through optical fiber 104 to detection unit 110. Optionally, the emitted light may be sent to reference arm 115 for creating an interference with a reference low coherency light for obtaining axial information (along a z-axis) on the illuminated particle 120-124 and/or illuminated vessel 116, for reproduction of a 3D image. Optionally, the axial component of the speed of the particle is determined.

At 805, emitted light is detected by detection unit 110. Detection unit 110 may include a spectrometer for measuring a distinct spectral band in the emitted light, a CCD camera for capturing a single-shot image of the emitted light, a single-element photo detector for measuring a discrete wavelength of the emitted light, or any combination thereof. Detection unit 110 generates an output to processing unit 112 based on the measurements.

At 806, processing unit 112 processes the output received from detection unit 110 and reproduces the image of illuminated particle 120-124 and/or illuminated vessel 116. Processing unit 112 performs all computations associated with flow cytometry, including substantially simultaneous determination of a number of particles, and other characteristics such as their type, size, shape, color, brightness, and the like.

At 807, display unit 114 displays information from processing unit 112. The information may be the 2D cross-sectional image of illuminated particle 120-124, illuminated vessel 116, body fluid 118, or any combination thereof, and optionally the 3D image. Optionally, flow cytometry information computed by processing unit 112 is displayed.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Referring now to the drawings, FIG. 9 schematically illustrates an imaging probe 901 used in an imaging system 900 for locating a vessel, according to an exemplary embodiment of the invention. Optionally, imaging probe 901 is used non-invasively to locate a relatively deep vessel on a living subject. In some embodiments, the vessel may be at a depth of up to 100 μm below a tissue surface. Optionally, the vessel may be at an even greater depth up to 200 μm. The vessel may include any type of blood vessel, and may be a capillary or an arteriole. Additionally or alternatively, imaging probe 901 may be used for performing in vivo SEFC. In some embodiments, imaging probe 901 is a handheld probe. Alternatively, imaging probe 901 is an endoscopic probe or a catheter probe.

Imaging probe 901 houses a detection unit 902 and a background light source 904. Detection unit 902 may include a CCD camera, CMOS camera, or any other type of image acquisition device known in the art sized for being housed in the imaging probe and adapted to detect backscattered background light. Background light source 904 may include a LED which produces a background light 906 which is green, or may optionally be any other suitable green light source known in the art. Optionally, background light source 904 may generate background light 906 of red color. As described below, the illumination using the background light may share an optical pathway and/or line of sight with an optical sensor used to analyze properties of the blood flow.

Imaging probe 901 is externally connected to an illuminating light source (not shown) in system 900 through an optical fiber 908 and through which an illuminating lighting 912 is fed to the imaging probe. Optionally, optical fiber 908 is a single-mode optical fiber. Imaging probe 901 is externally connected to a processing unit (not shown) through a second optical fiber 910 and through which illuminating light backscatter 913 is fed to the processing unit. Optionally, optical fiber 910 is a single-mode optical fiber. Optionally, fiber 910 is a multimode optical fiber.

In an exemplary embodiment of the invention, imaging probe 901 includes a common optical channel 930 interconnecting aperture 931 with combiner/splitter 916; an illuminating optical channel 934 interconnecting a beam splitter 915 with the combiner/splitter; and a background light optical channel 932 interconnecting a beam splitter 925 with the combiner/splitter; all three channels configured for handling illumination and backscattering lighting.

An example of imaging probe 901 operation may include combining green light 906 from background light source 904 with illuminating light 912 at beam combiner 916, collimating background light 906 and illuminating light 912 at collimator 918, diffracting illuminating light 912 at diffraction grating 920, and focusing by means of objective lens 922 spectrally dispersed illuminating light 912 and green light 906 to a transverse line on a portion of the vessel section. Diffraction grating 920 may in some embodiments be replaced with a combination of a mirror at 920, and a separate transmission diffraction grating, 920A. In further embodiments, diffraction grating 920 may be replaced by a mirror at 920, and a separate transmission diffraction grating 934A may be placed among the optical elements which comprise optical channel 934. A backscattered light from the tissue is captured by imaging probe 901 through objective lens 922 and may be collimated in collimator 924, split by beam combiner 916, with the backscattered background light 924 directed through beam splitter 926 into detector 902, and the backscattered illuminating light 913 directed through beam splitter 915 to optical fiber 910. In some embodiments, all optical components are stationary and are not mechanically movable. Alternatively, objective lens 922 may be mechanically moved for focusing illuminating light 912 and green light 906 to the transverse line.

Reference is now made to FIG. 10 which schematically illustrates an imaging probe 1001 used in an imaging system 1000 for locating a vessel, according to an exemplary embodiment of the invention. Optionally, imaging probe 1001 is used non-invasively to locate a relatively deep vessel on a living subject. Additionally or alternatively, imaging probe 1001 may be used for performing in vivo SEFC. In some embodiments, imaging probe 1001 is a handheld probe. Alternatively, imaging probe 1001 is an endoscopic probe or a catheter probe.

Imaging probe 1001 houses a detection unit 1002, a background light source 1004, and a processing unit 1005. Detection unit 1002 may include a CCD camera, CMOS camera, or any other type of suitable image acquisition device known in the art sized for being housed in the imaging probe, and may include a display for displaying a 2D image of the illuminated portion of the vessel and/or of the particles. Background light source 1004 may include a LED which produces a light 1006 which is green, or may optionally be any other suitable green light source known in the art. Optionally, background light source 1004 may generate light 1006 of red color. Processing unit 1005 may process data generated by detection unit 1002 responsive to detection of a backscattered light 1024, for generating the displayed image optionally on the display of detection unit 1002.

In an exemplary embodiment of the invention, imaging probe 1001 is externally connected to an illuminating light source and a processing unit (both not shown) in system 1000 through an optical fiber 1008 connected to an optical fiber connector 1009 in the probe. Optionally, optical fiber 1008 is a single-mode optical fiber.

In an exemplary embodiment of the invention, imaging probe 1001 includes a common optical channel 1030 interconnecting aperture 1031 with combiner/splitter 1016; an illuminating optical channel 1034 interconnecting optical fiber connector 1009 with the combiner/splitter; and a background light optical channel 1032 interconnecting a beam splitter 1026 with the combiner/splitter; all three channels configured for handling illumination and backscattering lighting.

An example of imaging probe 1001 operation may include combining green light 1006 from background light source 1004 with illuminating light 1012 at beam combiner 1016 following the lights having passed through lenses 1015, diffracting illuminating light 1012 at diffraction grating 1020, and focusing by means of objective lens 1022 spectrally dispersed illuminating light 1012 and green light 1006 to a transverse line on a portion of the vessel section. A backscattered light 1024 from the tissue is captured by imaging probe 1001 through objective lens 1022 and split by beam combiner 1016 with the background backscatter light through beam splitter 1026 into detector 1022, and the illuminating backscatter light going to optical fiber connector 1009. In some embodiments, all optical components are stationary and are not mechanically movable. Alternatively, objective lens 1022 may be mechanically moved for focusing illuminating light 1012 and green light 1006 to the transverse line.

Reference is now made to FIG. 11 which schematically illustrates an imaging probe 1101 used in an imaging system 1100 for locating a vessel, according to an exemplary embodiment of the invention. Optionally, imaging probe 1101 is used non-invasively to locate a relatively deep vessel on a living subject. Additionally or alternatively, imaging probe 1101 may be used for performing in vivo SFEC. In some embodiments, imaging probe 1101 is a handheld probe. Alternatively, imaging probe 1101 is an endoscopic probe or a catheter probe.

Imaging probe 1101 is externally connected to an illuminating light source and a processing unit (both not shown) in system 1100 through an optical fiber 1108 connected to an optical fiber connector 1109 in the probe. Optionally, optical fiber 1108 is a single-mode optical fiber. Additionally, imaging probe 1101 is externally connected to a background light source (not shown) in system 1100 through an optical fiber 1107 connected to an optical fiber connector 1109 in the probe. Optionally, optical fiber 1107 is a multi-mode optical fiber. Additionally, imaging probe 1101 is externally connected to a processing unit (not shown) in system 1100 through an optical fiber 1111 connected to an optical fiber connector 1109 in the probe. Optionally, optical fiber 1111 is an optical fiber bundle. In some embodiments, optical fiber bundle 1111 is connected to a spectrometer (not shown).

In an exemplary embodiment of the invention, imaging probe 1101 includes a common optical channel 1030 interconnecting aperture 1131 with combiner/splitter 1116; an illuminating optical channel 1134 interconnecting optical fiber connector 1109 and optical wire 1108 with the combiner/splitter; and a background light optical channel 1132 interconnecting a beam splitter 1126 with the combiner/splitter; all three channels configured for handling illumination and backscattering lighting. Imaging probe 1101 includes two separate optical channels which connect to beam splitter 1126, a background light channel 1136 connecting optical fiber 1107 to splitter 1126, and a background backscatter channel 1135 connecting optical fiber bundle 1111 to splitter 1126.

An example of imaging probe 1101 operation may include combining green light 1106 arriving through optical fiber 1107 with illuminating light 1012 arriving through optical fiber 1108 at beam combiner 1116 following the lights having passed through lenses 1105, diffracting illuminating light 1116 at diffraction grating 1120, and focusing by means of objective lens 1122 spectrally dispersed illuminating light 1112 and green light 1106 to a transverse line on a portion of the vessel section. A backscattered light 1124 from the tissue is captured by imaging probe 1101 through objective lens 1122 with the background backscatter light diverted by beam combiner 1116 through beam splitter 1126 and through lens 1105 into optical fiber bundle 1111. The backscatter illuminating light is split by beam splitter 1116 to optical fiber 1108. In some embodiments, all optical components are stationary and are not mechanically movable. Alternatively, objective lens 1122 may be mechanically moved for focusing illuminating light 1112 and green light 1106 to the transverse line.

Reference is now made to FIG. 12 which schematically illustrates an imaging probe 1201 used in an imaging system 1200 for locating a vessel, according to an exemplary embodiment of the invention. Imaging probe 1201 is similar to imaging probe 1101 in FIG. 11 with an additional feature of a handle 1220 for mechanically attaching the probe to a stationary fixture, thereby preventing its movement. This feature optionally allows for better maintaining the probe focused on the transverse line on the portion of the vessel section. In some embodiments, handle 1120 is affixed to a body section of a live subject being imaged, for example, to a leg, an arm, or on the body.

Optionally, when attached to the body portion, relative moment between the probe and the tissue is substantially reduced. Although handle 1220 is shown as part of imaging probe 1201, the handle may readily be included in any of the embodiments of the imaging probes described herein.

Reference is now made to FIG. 13 which schematically illustrates an imaging probe 1301 used in an imaging system 1300 for locating a vessel, according to an exemplary embodiment of the invention. Imaging probe 1301 is similar to imaging probe 1101 in FIG. 11 with an additional feature of a vacuum suction mechanism 1302 which substantially minimizes tissue movement when operated by suctioning the tissue against the probe. Optionally, vacuum suction mechanism 1302 provides a low pressure sectional force, and may be used alternatively or additionally to the handle 1220 or with other probe designs.

Vacuum suction mechanism 1302 may include a plunger 1304 positioned inside a chamber 1306 connecting through a conduit 1308 to a suction cap 1310. Suction cap 1310 is placed around an opening 1312 bordering an objective lens 1322 and through which illuminating light and background light are transmitted to the vessel. Suction cap 1310 optionally includes an opening or a section with optical transparency. Alternatively, imaging is to the side of the opening, 1314 through which the transmitted light and the backscattered light may pass, optionally with minimal interference, in and out of the imaging probe. Suction cap 1310 further includes openings 1312 which align with conduit 1308 and through which air may flow in and out of the conduit. For creating a vacuum for drawing the tissue toward imaging probe 1301, plunger 1304 is pulled in a proximal direction, thereby drawing the tissue towards the probe. Pushing plunger 1304 in a distal direction will remove the vacuum. In some embodiments, vacuum suction mechanism 1302 may be electrically powered, and may include AC and/or DC. Alternatively, vacuum suction mechanism 1302 may be replaced by other means for maintaining the tissue relatively, for example, by temporarily adhering the tissue to the imaging probe with an adhesive or the like. In some embodiments, the adhesive is part of the probe and the probe or its casing is disposable following one or repeated uses.

In an exemplary embodiment of the invention, fixation techniques are used to support continuous monitoring, for example, fixation is provided which allows sensing for, for example, 1, 5, 10, 30, 60, 120 or smaller or intermediate number of seconds, or more, for example, 3 minutes, 5 minutes, 15 minutes, up to an hour, 1-10 hours and/or during bed rests and/or movement or exercise. Data logging for such periods of time may be provided in a control circuitry (e.g., using a memory and/or processing unit thread).

In an exemplary embodiment of the invention, the probe includes a strap, an elastic band or a place to attach an adhesive band, to allow compressive fixation to tissue. This may be in addition to or instead of an adhesive layer between the probe and the tissue.

Reference is now made to FIG. 14 which schematically illustrates an imaging probe 1401 used in an imaging system 1400 for locating a vessel, according to an exemplary embodiment of the invention. Optionally, imaging probe 1401 is used non-invasively to locate a relatively deep vessel on a living subject. Additionally or alternatively, imaging probe 1401 may be used for performing in vivo SEFC. In some embodiments, imaging probe 1401 is a handheld probe. Alternatively, imaging probe 1401 is an endoscopic probe or a catheter probe.

Imaging probe 1401 is configured for receiving a background light 1406 and for transmitting a backscattered light 1426 through a same optical channel. Imaging probe 1401 is externally connected to an illuminating light source (not shown) in system 1400 through an optical fiber 1408 for receiving illuminating light 1412. Optionally, optical fiber 1408 is a single-mode optical fiber. Additionally, imaging probe 1401 is externally connected to a background light source (not shown) and to a processing unit (not shown) in system 1400 through an optical fiber 1411. Optionally, optical fiber 1411 is an optical fiber bundle. Optionally, optical fiber bundle 1411 is connected to a spectrometer (not shown). Optionally, the functions of the spectral dispersing element and the beam combining element are combined in one combining-dispersing element 1420, which may be a transmissive diffraction grating, and accordingly both combines and spectrally disperses said background light 1406 and said illuminating light 1412 before they are directed to the probe objective 1422.

Above have been described several embodiments of imaging probes which may be included in a system for locating vessels. The described embodiments are exemplary and an ordinary person skilled in the art may find that there are many ways of implementing the features described herein, for example, other designs may be used which integrate a vessel finding optical sensor with a vessel analyzing optical sensor, for example, in fixed relationship and with shared optical pathways and/or lines of sight, and/or as part of a microscope.

Reference is made to FIG. 15 which illustrates a flow chart of an exemplary method for locating a vessel, in accordance with an embodiment of the present invention. An ordinary person skilled in the art may appreciate that the exemplary method described herein may be implemented in other ways, forms, and/or manners.

At 1501, an operator of the system for locating a vessel optionally sets up the probe for use, for example, connects the imaging probe to an illumination light source and a background source by connecting respective wave guides to the probe. Illumination light and background light are transmitted over optical guides to the imaging probe.

In some embodiments, the imaging probe may include an endoscope or a catheter. Illumination light may be a broadband light or a wavelength-swept light. Background light may be green wide-field light or a red wide-field light. The optical fiber for the illumination light may be a single-mode optical fiber. The optical fiber for the background light may be a multi-mode optical fiber. Alternatively the background light is transmitted over a fiber bundle. In some embodiments, the background light is generated by the imaging probe.

At 1502, in operation in the imaging probe the illumination light is collimated by a collimator and spectrally diffracted by a diffracted grating. Optionally, illumination light is not collimated. The illumination light is combined with the background light. Optionally, the background light is collimated.

At 1503, the system operator approximates the imaging probe to a subject's tissue for illuminating a portion of a vessel. Optionally, the vessel is relatively deep, for example, at a depth up to 200 μm. In some embodiments, the imaging probe substantially minimizes movement of the subject's tissue relative to the imaging probe. Alternatively, the operator adheres the imaging probe to the tissue using an adhesive. In some embodiments, the operator reduces movement by pressing the probe against the tissue.

Optionally, an improved view of the cells is obtained by the pressing. Optionally, the focus is improved by such pressing. The background light is partially or wholly absorbed by the particles in the vessel. Backscattering light is produced by the illuminated portion of the vessel.

In an exemplary embodiment of the invention, the operator views an image and adjusts the probe until the image includes a blood vessel. A target area of the probe is optionally aligned with the vessel, for example, by moving the probe or by motorized movement of optical line of sight changing elements in the probe. In an exemplary embodiment of the invention, the target area is a line and is aligned to be perpendicular to an axis of the blood vessel. Optionally, pressure is applied to shape the blood vessel, for example, to compress it by 20%, 40%, 60% or greater or intermediate amounts and/or to cause certain flow characteristics therein. In an exemplary embodiment of the invention, the vessel is compressed to a flat oval shape forcing the cells to align with their narrow dimension toward the flow direction. Optionally, the shape of the vessel is sensed using the sensing ability of the probe and provided as feedback to the operator.

For efficient detection of WBCs, the depth of focus of the imaging probe is optionally positioned only a few microns below the front wall of post-capillary venules, where marginated WBCs are abundant and RBCs are rarely seen. In this location, passing WBCs may be detected and automatically registered by plotting the total scattered power as a function of time (FIG. 20a). In an exemplary embodiment of the invention, use is made of the measurable WBC flux increasing with vessel diameter (FIG. 20b).

Optionally, the vessel size is selected by the user to match the desired viewing.

Optionally or alternatively, the system corrects measured parameters based on the vessel size, for example, using a correction table. Optionally, the display includes an indication of vessel size to assist the operator in selecting a suitable vessel and/or selecting correct processing parameters.

In an exemplary embodiment of the invention, the searching for a vessel includes determining a desired vessel size and searching for a vessel of that size, for example, a capillary or a small arteriole. In an exemplary embodiment of the invention, the vessel size is, for example, between 1 and 50 microns in diameter, for example, between 2 and 20 microns in diameter.

At 1504, the imaging probe collects (captures) the backscattered light which is then sent through an optical fiber to the detection unit. Alternatively, the detection unit is in the imaging probe or other detection mechanisms are used to collect and/or detect light by the probe. Optionally, the backscattered light may be sent to a reference arm for creating an interference with a reference low coherency light for obtaining axial information (along a z-axis) on the illuminated vessel and/or illuminated particles, for reproduction of a 3D image. Optionally, the axial component of the speed of the particle is determined. In some embodiments, the detection unit may include a spectrometer for measuring a distinct spectral band in the backscatter light, a CCD camera for capturing a single-shot image of the backscattered light against the contrast background, a single-element photo detector for measuring a discrete wavelength of the emitted light, or any combination thereof. The detection unit generates an output to the processing unit based on the measurements. Optionally, the output is sent from the image processing device through an optical guide to the processing unit. Alternatively, the processing unit is located on the image processing device together with the detection unit.

At 1505, the processing unit processes the output received from detection unit and reproduces the image of the illuminated vessel. The processing unit performs all computations associated with imaging the vessel. Optionally, computations associated with flow cytometry, including substantially simultaneous determination of a number of particles, and other characteristics such as their type, size, shape, color, brightness, and the like are performed. In an exemplary embodiment of the invention, the target area on which such computations are performed is shown as a red line overlaid on a green image showing the blood vessels. Other colors and/or indication may be used as well.

At 1506, the display unit displays information from the processing unit. The information may be the 2D cross-sectional image of the portion of the vessel and/or of the particles, and optionally the 3D image. The operator views the images on the display to view the particles. Optionally, the operator views the results of the computation associated with flow cytometry.

Reference is now made to FIG. 22 which schematically illustrates an imaging probe 2302 used within an imaging system for locating, for example, a vessel 2315 in a region of tissue 2316, according to an exemplary embodiment of the invention, and also used within an imaging system for imaging and determining properties of one or more of, for example, a located vessel, and particles, tissue, and body fluid associated with the located vessel.

Optionally, imaging probe 2302 is used non-invasively to locate a relatively deep vessel on a living subject. Additionally or alternatively, imaging probe 2302 may be used for performing in vivo SEFC, which may be interferometric SEFC, including high-speed interferometric SEFC, such as is described in relation to FIG. 8B. In some embodiments, imaging probe 2302 is a hand-held probe. Alternatively, imaging probe 2302 is an endoscopic probe or a catheter probe.

In an exemplary embodiment of the invention, imaging probe 2302 includes a common optical channel 2328 inter-connecting the imaged region of tissue 2316 and/or vessel 2315 with beam combiner/splitter 2326; an illuminating optical channel 2330 interconnecting the coupling point of the illuminating light optical fiber 2310 with beam combiner/splitter 2326; and a background light optical channel 2332 inter-connecting a beam splitter 2324 with beam combiner/splitter 2326. All three channels may be configured for handling illumination and backscattering lighting.

In some embodiments of the invention, the imaging probe 2302 houses a detection unit 2304 and a background light source 2306. Detection unit 2304 may include a CCD camera, CMOS camera, or any other type of image acquisition device known in the art sized for being housed in the imaging probe and adapted to detect backscattered background light. Background light source 2306 may include a LED which produces a background light 2308 which is green, or may optionally be any other suitable green light source known in the art. Optionally, background light source 2306 may generate background light 2308 of red color.

Through an optical fiber 2310, imaging probe 2302 is externally connected to an illuminating light source (not shown), which is appropriate to the chosen embodiment of the elements of the system which perform particle imaging and characterization. From optical fiber 2310, illuminating light 2312 is fed to the imaging probe. Optionally, optical fiber 2310 is a single-mode optical fiber. After collimation by collimator 2313, the light is spread by a wavelength dispersing element, 2314, which may be a transmission diffraction grating. In some embodiments of the invention, a telescopic relay arrangement is provided which may be comprised of two achromatic lenses 2318A and 2318B guides the light to the beam combiner/splitter 2326. By the use of the telescopic relay, the uniformity of the field of view may be improved.

An example of imaging probe 2302 operation may further include combining green light 2308 from background light source 2306 with illuminating light 2312 at beam combiner/splitter 2326. The light may be focused by means of objective lens 2320, directing spectrally dispersed illuminating light 2312 to a transverse line on a portion of the vessel section, and green light 2308 to a region including that line. In an exemplary embodiment of the invention, light returned or emitted from the tissue is captured by imaging probe 2302 through objective lens 2320. It may be split by beam combiner/splitter 2326. The returned or emitted background light may be directed through beam combiner/splitter 2326 into detector 2304. The returned or emitted illuminating light may be directed through to optical fiber 2310, after which it is directed to other parts of the system, which may include elements for interferometric or spectral imaging of the light, as described, for example, with regard to exemplary systems such as 2200.

In some embodiments, all optical components are stationary and are not mechanically movable. Alternatively, objective lens 2320 may be mechanically moved for focusing illuminating light 2312 and green light 2308 to the transverse line.

Reference is made to FIG. 16 which schematically illustrates an imaging system 1600 for in vivo imaging, according to an exemplary embodiment of the invention.

Broadband light from a fiber-coupled super luminescent diode array 1602 (Superlum S840-B-I-20, 840 nm central wavelength, 50 nm bandwidth) was collimated into a 2.5 mm diameter beam using an aspheric lens 1606 (11 mm focal length), expanded using a 3.75× beam expander comprising lenses 1613 and 1614, and focused onto a transverse spectral line using a transmission diffraction grating 1608 (1200 l/mm, Wasatch photonics) and a water immersion objective lens 1612 (60×, NA=1.2, Olympus). Imaging depth inside the tissue 1628 was adjusted by manually threading a protective aluminum cap 1629 with an attached 0.17 mm thick cover glass which was in contact with the tissue. The gap between the objective front element and the cover glass was filled with water. Backscattered light from the tissue was collected and collimated by the illumination optics comprising lenses 1614 and 1613 in a confocal geometry, split by a 50:50 cubic beam splitter 1616, coupled to a single-mode collection fiber and directed to a home-built spectrometer 1618 with a high-sensitivity electron-multiplying CCD camera (DU970N, Andor, 1300 lines/s). For high acquisition rates which were required for imaging rapid cell flow, a faster CCD camera (Aviiva EM4, e2v) was used, allowing acquisition rates of up to 71,000 lines/s. The lateral resolution of the imaging probe was 0.7 µm (edge response, FWHM), the axial resolution was 1.5 µm (FWHM, measured by axially scanning a reflective surface across the focal volume), and the lateral field of view in the wavelength axis was 110 µm. The total power incident on the sample was approximately 7 mW.

The relatively small field of view of the confocal spectrally encoded line may impose a difficulty in identifying blood vessels deep below the tissue surface. In an exemplary embodiment of the invention, the location of blood vessels is assisted by using an additional wide-field green imaging channel that was added to the probe and that shares the same objective lens. A beam from a light-emitting diode 1620 (M530L2, Thorlabs, 530 nm central wavelength) was collimated and coupled to the imaging channel using a dichroic mirror 1621 (t680dcspxr, Chroma technology). The light backscattered from the tissue was imaged using a two-dimensional CCD camera 1624 (UI-2220, IDS) at 20 frames/s. Blood vessels were observed at high contrast within a field of view of 400×300 µm$^2$ as dark regions on a bright background due to the high relative absorption of the green light by hemoglobin. A pair of crossed polarizers 1623A and 1623B was used to reject surface reflections to further enhance contrast.

Data from both the illuminating light and green channels were simultaneously sampled and displayed by a personal computer 1626 in real-time, using a custom built software (LabVIEW, National Instruments).

In some embodiments of the invention the display is replaced and/or enhanced by an automated system which rotates and/or aligns a target area with a blood vessel, optionally using image processing techniques to detect the blood vessel (e.g., using an on-probe processor).

Optionally, instead of a 2D imager, a scanning 1D imager is used to detect the blood vessel.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, without those elements.

Various embodiments and aspects of the present invention as delineated hereinabove and as claimed in the claims section below find experimental support in the following examples.

EXAMPLES

Reference is now made to the following example which, together with the above descriptions, illustrates some embodiments of the invention in a non-limiting fashion. It should be noted this example provides also features and parameter values which may be used with others of the embodiments described above.

The inventors conducted a study which included applying an embodiment of the method and the system for performing imaging in vivo and in vitro of vessels. Following are described the experimental set-up and the results obtained. It should be noted that the measurement and calculation methods described therein may be used with various exemplary embodiments of the invention or replaced by other methods.

Imaging System

Testing was conducted using the imaging system described in FIG. 16.

In Vivo Imaging

A healthy volunteer (healthy male, age 32) was seated in a high chair with a padded chin rest and placed his lower lip against the imaging probe. Blood vessels at depths ranging from 70 μm to 200 μm under the tissue surface were located using the live view imaging of the green channel CCD. Each continuous imaging session was limited to less than 30 s, primarily due to subject motion.

In Vitro Imaging

Blood for in vitro imaging was extracted from healthy donors by venipuncture. 5000 units/ml Heparin (Fresenius) were added to prevent coagulation. Diluted whole blood (1:5) was prepared by adding phosphate buffered saline with 2% bovine serum albumin. Blood components were separated by density gradient centrifugation (Lymphoprep™ Axis-shield). The mononuclear cell fraction was incubated for 1 hr at 37° C. humidified incubator followed by collection of the non-adherent lymphocytes. Polymorphonuclear cells were purified by using an RBC lysis solution (Miltenyi Biotec). All WBCs were resuspended in autologous plasma which was diluted (1:1) with phosphate buffered saline. In vitro SEFC imaging of the different cell samples was performed at average flowing speed of 0.4 mm/s (Syringe pump 11 Elite, Harvard Apparatus) through a 5 mm×0.8 mm rectangular plastic flow chamber (μslide-I, Ibidi). For standard fluorescence images, cell nuclei were stained with 1 mg/ml Hoechst 33342 (Sigma Aldrich) and imaged using a 20× objective lens (Nikon).

Image and Data Analysis

The average flow velocity $v_{av}$ was calculated according to:

$$v_{av}=d_{av}/t_{av},$$

where $d_{av}$ denotes the average lateral size of the RBCs and $t_{av}$ denotes their average passage time across the spectrally encoded line. Both $d_{av}$ and $t_{av}$ were calculated following manual segmentation of the cells in the raw image with a custom software (Matlab, Mathworks). The concentration of WBCs in a vessel was calculated according to:

$$C_{WBC}=N/(\pi R^2 v_{av} T),$$

where N denotes the total number of observed cells during a total imaging time T, and R denotes the estimated radius of the vessel. Assuming that cell detection follows Poisson statistics, the estimated error $\sigma_{WBC}$ in determining the concentration is given by $\sigma_{WBC}=N_{1/2}/(\pi R^2 v_{av} T)$.

The fractional area occupied by RBCs in a single image was estimated by calculating the ratio between the total manually segmented cells area and the total vessel area (Photoshop CS3, Adobe).

Results

In Vitro Imaging

Scattering by flowing RBCs and a strong reflection from the glass surface of the flow chamber allowed imaging of whole blood at depths of less than 5 μm below the chamber wall. Clear images of flowing RBCs were obtained only after blood dilution which allowed significant improvement in image quality and depth (FIG. 17a). The nearly random orientation of RBCs in the flow of the diluted blood revealed a wide diversity of shapes and brightness levels in the SEFC images. RBCs which were oriented with their symmetry axis pointing toward the objective lens showed a few bright concentric rings with typical diameters of 6-8 μm, caused by interference of light reflections from the front and back plasma membranes (FIG. 17a, insets). Slanted and/or deformed RBCs appeared smaller and somewhat dimmer with various shapes including half circles, ellipses, and sharp curves.

WBCs appeared distinctively different from RBCs, with a larger size and a bright, speckled appearance. In order to study the appearance of different WBC subtypes in the SEFC image, granulocytes and lymphocytes were isolated from a whole blood sample, imaged within a flow chamber (FIG. 17b) and compared to fluorescently labeled wide-field images of cells from the same group. Granulocytes were characterized by a pronounced, high intensity speckled appearance and multi-lobed nuclei visible as darker regions within the cells, while lymphocytes were much fainter with a more uniform (although still speckled) appearance. These two cell populations, while overlapping in diameter (FIG. 17c) could be differentiated simply by plotting the integrated intensity and the measured size of each cell (FIG. 17d).

In Vivo Imaging

Micro vessels approximately 70 μm below the surface of the lower lip of a human volunteer were first located using the real-time green channel imager (FIG. 18a, inset). An SEFC image which was registered with the green image and captured from the location marked by a dashed red line in the inset, revealed a bright, dense population of blood cells as they crossed the spectral line. Three digital magnification steps (in the time axis only) of the raw image (FIG. 18a-d, top-to-bottom panels) reveal the shapes and geometries of individual flowing cells. Light scattered from the vessel walls and from the surrounding tissue formed constant horizontal streaks, indicative of the relatively fixed orientation of the probe with respect to the tissue during the measurement.

A best balance between image quality and number of visible cells was obtained 2-4 μm below the front vessel wall.

In several occasions, a better view of the cells could be gained by applying a slight pressure with the probe on the tissue, deforming the blood vessel into a flat oval shape and forcing the cells to align with their narrow dimension toward the flow direction (FIG. 19a). Using this technique, the average diameter of the RBCs was measured to be 6.6±0.7 µm (FIG. 19b), in agreement with ex vivo cell size measurements [V. Hoffbrand, P. Moss, and J. Pettit, *Essential Hematology* (Blackwell, Malden, Mass., 2006)].

In vivo images (FIGS. 18a-d and 19a) provide direct means for estimating the hematocrit level of a patient. This essential parameter could be calculated by measuring the fractional area occupied by RBCs in the raw image; in n=6 different vessels (see FIG. 19c for a typical vessel) with diameters ranging from 7 µm to 20 µm, the RBC fractional area was 0.47±0.05, which is in a good agreement with the expected hematocrit of an adult healthy male. Individual RBCs could also be visualized in smaller capillaries (~5-8 µm diameter), in which single-file flow enabled the identification and counting of practically all cells flowing through the vessel (FIG. 19d).

Identification of WBCs in vivo in view of their low concentration in healthy subjects may be assisted by using longer imaging periods for gaining sufficient data. For efficient detection of WBCs, the depth of focus of our imaging probe was positioned only a few microns below the front wall of post-capillary venules, where marginated WBCs are abundant [G. W. Schmid-Schönbein, S. Usami, R. Skalak, and S. Chien, "The interaction of leukocytes and erythrocytes in capillary and postcapillary vessels," Microvascular Research 19, 45-70 (1980)] and RBCs are rarely seen. In this location, passing WBCs could be detected and automatically registered by plotting the total scattered power as a function of time (FIG. 20a). The measurable WBC flux increases with vessel diameter, as shown by measuring the flux in n=10 different vessels (FIG. 20b).

An average WBC diameter of 9.4±1.4 µm was measured (FIG. 20c), in agreement with our in vitro measurements. WBCs rolling on the endothelial vessel wall (FIG. 21A) and small aggregates of WBCs (FIG. 21B) were also observed on numerous occasions.

In small capillaries whose diameter is roughly that of a WBC, all passing WBCs could be easily viewed and counted. Most WBCs were viewed with a characteristic downstream RBC depleted region and an upstream accumulation of RBCs [G. W. Schmid-Schönbein, S. Usami, R. Skalak, and S. Chien, "The interaction of leukocytes and erythrocytes in capillary and postcapillary vessels," Microvascular Research 19, 45-70 (1980)] (FIG. 21C). A continuous 9.2 s long measurement across a 10 µm diameter capillary revealed a total of 12 cells, which correspond to a rough estimate of 8800±2500 WBCs/µL—within the normal range for healthy adults [V. Hoffbrand, P. Moss, and J. Pettit, *Essential Hematology* (Blackwell, Malden, Mass., 2006)]. Longer measurement periods would significantly increase the accuracy of this estimate, and may allow continuous tracking of WBC count in critical care patients which are sensitive to sudden inflammation. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. An imaging probe for locating a target blood vessel located under a portion of a tissue surface, the imaging probe located outside the portion of the tissue surface, the imaging probe comprising:
    an objective lens;
    a background imaging channel comprising a background light source configured to illuminate with background light a tissue region located under the portion of the tissue surface through the objective lens, using widefield illumination comprising a background light component having a substantially high susceptibility to absorption by particles in said portion of the target blood vessel; and
    an illuminating optical channel comprising an illuminating light source and an illumination light processing unit, respectively configured to illuminate with illuminating light and image through the objective lens, along a focal line within the tissue region;
    wherein the illuminating optical channel also comprises an optical arrangement configured to direct light backscattered from the focal line to the illumination light processing unit;
    wherein the illumination light processing unit is configured to decode position from illuminating light backscatter returning from the focal line, the focal line located under the portion of the tissue surface;
    wherein the background light and the illuminating light both illuminate from the objective lens through an optically transparent surface of the imaging probe, wherein said imaging is through said optically transparent surface, and wherein said optically transparent surface is configured to be in contact with the portion of the tissue surface under which the target blood vessel is located; and
    wherein, in addition to the illuminating optical channel which is dispersed across the focal line, said objective lens is adjustable relative to the optically transparent surface, to move an optical line of sight of confocal imaging of the background imaging channel and the illuminating optical channel, such that said imaging probe is configured to image at least a portion of the blood vessel located under the portion of the tissue surface.

2. The imaging probe according to claim 1, wherein said illuminating light source is coupled to a dispersing element to disperse the illuminating light along the focal line, said imaging probe including an arrangement of lenses comprising a telescopic light relay between said dispersing element and a beam combiner/splitter proximal to the target blood vessel.

3. The imaging probe according to claim 1, wherein said illuminating light source is coupled to a dispersing element to disperse the illuminating light along the focal line, where said dispersing element includes a combining element.

4. The imaging probe of claim 1, wherein said optical arrangement configured to direct light backscattered from the focal line to the illumination light processing unit comprises a collimator.

5. The imaging probe of claim 1, wherein said illuminating light source comprises a broad bandwidth light source, said imaging probe further including a detection unit comprising a spectrograph.

6. The imaging probe of claim 5, wherein said broad bandwidth light source is configured to illuminate with a broad bandwidth light and wherein said background light component has a shorter wavelength than that of the backscattered broad bandwidth light.

7. The imaging probe of claim 5, wherein said broad bandwidth light source is configured to spectrally disperse a broad bandwidth light component of said illuminating light along an axis including the target blood vessel.

8. The imaging probe of claim 1, wherein said illuminating light source comprises a wavelength-swept light source, said imaging probe further including a detection unit comprising a single-element photo detector.

9. The imaging probe of claim 8, wherein said wavelength-swept light source is configured to spectrally disperse a wavelength-swept light component of said illuminating light along an axis including the target blood vessel.

10. The imaging probe of claim 1, wherein said illuminating light source comprises multiple light sources with different wavelengths, said imaging probe further including a detection unit comprising a spectrograph.

11. The imaging probe of claim 1, wherein said objective lens is adjustable to move the optical line of sight along the tissue surface.

12. The imaging probe of claim 1, wherein said illumination light processing unit is configured to determine a location, a speed of flow, a size, a length, a shape, a color, an orientation, or a brightness of a particle, a number of particles, or any combination thereof, in the target blood vessel.

13. The imaging probe of claim 1, wherein said illumination light processing unit is configured to determine an absorption over the target blood vessel to obtain spectroscopic absorption measurements.

14. The imaging probe of claim 1 wherein the target blood vessel is a capillary, a venule or an arteriole.

15. The imaging probe of claim 14 wherein the target blood vessel is located at a depth of up to 200 μm below the tissue surface.

16. The imaging probe of claim 1, wherein said illumination light processing unit is configured to detect particles that flow across the focal line.

17. The imaging probe of claim 1, wherein at least one of:
said objective lens is movable to adjust at least one of an imaging depth and a lateral position of said objective lens relative to said optically transparent surface; and
said objective lens is adjustable to focus said illuminating light on an imaged portion of the blood vessel.

18. The imaging probe of claim 1, wherein the background light source is configured to illuminate a sub-region of the region after passage through a first polarizer of a pair of crossed polarizers, and wherein said imaging probe includes a detection unit configured for detecting the backscattered light after the backscattered background light is passed through a second polarizer of the pair of crossed polarizers.

19. The imaging probe of claim 1, wherein the optical line of sight of confocal imaging comprises a cross-sectional 2D particle image wherein the focal line is sampled at a frequency above 10 KHz.

20. The imaging probe of claim 1, wherein said imaging probe is configured to perform said imaging of at least a portion of the blood vessel from a position at a distance from the target blood vessel.

21. The imaging probe of claim 1, wherein the relative scanning position between the optically transparent surface and the objective lens is adjustable to define a depth of confocal imaging through the objective lens.

22. The imaging probe of claim 21, wherein the depth of confocal imaging is adjustable by adjusting a vertical position of said objective lens relative to said optically transparent surface.

23. The imaging probe of claim 1, wherein a gap between the objective lens and the optically transparent surface is filled with water.

24. The imaging probe of claim 1, wherein said optically transparent surface is configured to be pressed against the surface of the tissue to further improve a focus of said confocal imaging through the objective lens.

25. The imaging probe of claim 1, wherein said optically transparent surface is configured to be held in a fixed position relative to the portion of the tissue surface whereby said optically transparent surface is configured to be held in contact with the tissue surface by one of a vacuum and an adhesive.

26. The imaging probe of claim 1, wherein the portion of the tissue surface is a target portion of the tissue surface;
wherein said background light component is configured to be non-invasively moved to a second or further sub-region located under the portion of the tissue surface when no higher-absorbing region corresponding to said portion of the vessel is positioned along the focal line.

27. The imaging probe of claim 1, wherein the illumination light source is configured to spectrally disperse the illuminating light across the focal line and to image the focal line such that the light used to image from the focal line spectrally encodes position across the focal line.

* * * * *